US012788510B2

(12) United States Patent
Gordon et al.

(10) Patent No.: US 12,788,510 B2
(45) Date of Patent: Nov. 10, 2026

(54) HYBRID, DIRECT-CONTROL AND ROBOTIC-ASSISTED SURGICAL SYSTEM

(71) Applicant: REVOLVE SURGICAL INC., Toronto (CA)

(72) Inventors: Peter Alexander Gordon, Toronto (CA); Peter Francis, Toronto (CA); Rami Saab, Toronto (CA)

(73) Assignee: Revolve Surgical Inc., Toronto (CA)

( * ) Notice: Subject to any disclaimer, the term of this patent is extended or adjusted under 35 U.S.C. 154(b) by 769 days.

(21) Appl. No.: 17/642,882

(22) PCT Filed: Sep. 14, 2020

(86) PCT No.: PCT/CA2020/051237

§ 371 (c)(1),
(2) Date: Mar. 14, 2022

(87) PCT Pub. No.: WO2021/046658

PCT Pub. Date: Mar. 18, 2021

(65) Prior Publication Data

US 2022/0395339 A1 Dec. 15, 2022

Related U.S. Application Data

(60) Provisional application No. 62/900,471, filed on Sep. 14, 2019.

(51) Int. Cl.
*A61B 34/32* (2016.01)
*A61B 34/20* (2016.01)
(Continued)

(52) U.S. Cl.
CPC ...... *A61B 34/32* (2016.02); *A61B 2034/2059* (2016.02); *A61B 2034/302* (2016.02); *A61B 2090/5025* (2016.02); *A61B 2090/508* (2016.02)

(58) Field of Classification Search
CPC ............ A61B 34/32; A61B 2034/2059; A61B 2034/302; A61B 2090/5025;
(Continued)

(56) References Cited

U.S. PATENT DOCUMENTS 5,397,323 A * 3/1995 Taylor .................... A61B 34/71
901/41
5,587,937 A 12/1996 Massie et al.
(Continued)

FOREIGN PATENT DOCUMENTS

CN 102469995 A 5/2012
CN 104224328 A 12/2014
(Continued)

OTHER PUBLICATIONS

Wikipedia, "Center of Mass," https://en.wikipedia.org/wiki/Center_of_mass, accessed Jun. 9, 2025 (Year: 2025).*
(Continued)

*Primary Examiner* — Lynsey C Eiseman
*Assistant Examiner* — Christopher J Mutchler
(74) *Attorney, Agent, or Firm* — Aurora Consulting LLC; Albert Du; Ashley Sloat

(57) ABSTRACT

A hybrid, direct-control and robotic-assisted surgical system may have a stabilizing apparatus configured to at least partially support the weight of the surgical device and having comprising a device attachment unit configured to removably receive a surgical device having an elongate shaft and a distal tip. The stabilizing apparatus can be configured to constrain movement of the device attachment unit about a remote centre of motion. A handle may be mechanically attached to the device attachment unit and manual, Cartesian movement of the handle may results in corresponding Cartesian movement of the distal tip of the surgical device. A robotic assist system may include a sensor assembly con-
(Continued)

figured to monitor at least a first attribute of the handle and generate a corresponding sensor signal, a controller communicably linked to the sensor assembly to receive the sensor signal and generate a corresponding primary control signal and a powered actuation unit communicably linked to the controller to receive the primary control signal and configured to actuate an end effector of the surgical device received in the device attachment unit based on the primary control signal.

11 Claims, 35 Drawing Sheets

(51) Int. Cl.
*A61B 34/30* (2016.01)
*A61B 90/50* (2016.01)

(58) Field of Classification Search
CPC ... A61B 2090/508; A61B 34/37; A61B 34/74; A61B 34/71; A61B 34/30; A61B 90/50
See application file for complete search history.

(56) References Cited

U.S. PATENT DOCUMENTS 5,792,135 A 8/1998 Madhani et al.
5,820,623 A 10/1998 Ng
6,676,669 B2 1/2004 Charles et al.
6,702,805 B1 3/2004 Stuart
6,853,879 B2 2/2005 Sunaoshi
6,889,116 B2 5/2005 Jinno
7,021,173 B2 4/2006 Stoianovici et al.
7,454,268 B2 11/2008 Jinno
7,594,912 B2 9/2009 Cooper et al.
7,905,234 B2 3/2011 Jinno et al.
8,123,675 B2 2/2012 Funda et al.
8,414,475 B2 4/2013 Sholev
8,562,594 B2 10/2013 Cooper et al.
8,603,078 B2 12/2013 Stefanchik et al.
8,641,700 B2 2/2014 Devengenzo et al.
8,702,590 B2 4/2014 Sholev
8,734,312 B2 5/2014 Conner et al.
8,831,782 B2 9/2014 Itkowitz
8,911,429 B2 12/2014 Olds et al.
8,961,537 B2 2/2015 Leung et al.
9,027,431 B2 5/2015 Tang et al.
9,339,344 B2 5/2016 Schena et al.
9,545,288 B2 1/2017 Morash
9,649,020 B2 5/2017 Finlay
9,655,614 B2 5/2017 Swensgard et al.
9,788,903 B2 10/2017 Kim et al.
9,883,880 B2 2/2018 Malkowski et al.
9,999,473 B2 6/2018 Madhani et al.
10,251,532 B2 4/2019 Schara et al.
10,258,419 B2 4/2019 Auld et al.
10,299,821 B2 5/2019 Shelton, IV et al.
10,426,321 B2 10/2019 Sholev
10,617,561 B2 4/2020 Meenink
10,639,066 B2 5/2020 Vidal et al.
10,813,704 B2 10/2020 Kostrzewski et al.
2004/0162564 A1 8/2004 Charles et al.
2004/0222023 A1 11/2004 Haci et al.
2006/0253109 A1 11/2006 Chu
2006/0259019 A1 11/2006 Sanchez et al.
2008/0091066 A1 4/2008 Sholev
2009/0292299 A1 11/2009 Cooper et al.
2010/0185211 A1 7/2010 Herman et al.
2011/0022229 A1* 1/2011 Jang ........................ B25J 13/02 901/41
2012/0118098 A1 5/2012 Doyle et al.
2012/0158014 A1 6/2012 Stefanchik et al.
2012/0265071 A1 10/2012 Berke
2013/0039732 A1 2/2013 Brewer et al.
2013/0053866 A1* 2/2013 Leung .................... B25J 9/1689 901/23
2013/0131867 A1 5/2013 Olds et al.
2014/0039314 A1 2/2014 Stoianovici et al.
2014/0222023 A1 8/2014 Kim et al.
2016/0100900 A1 4/2016 Madhani et al.
2017/0086932 A1 3/2017 Auld et al.
2017/0303957 A1 10/2017 Vidal et al.
2018/0200009 A1 7/2018 Stefanchik et al.
2019/0223967 A1 7/2019 Abbott et al.
2019/0239972 A1* 8/2019 Chassot ............. A61B 18/1442
2019/0262089 A1 8/2019 Marshall et al.

FOREIGN PATENT DOCUMENTS

CN 108042208 A 5/2018
CN 109091232 12/2018
EP 0640319 B1 6/1997
EP 2208463 A1 7/2010
EP 2384715 B1 7/2015
JP 2005168820 A 6/2005
JP 2006061272 3/2006
KR 101304280 B 10/2008
KR 101483078 B1 1/2015
WO 2011002215 A2 1/2011
WO 2012020386 A1 2/2012
WO 2021046657 A1 3/2021
WO 2021046658 A1 3/2021

OTHER PUBLICATIONS

Wikipedia, "Revolute Joint," https://en.wikipedia.org/wiki/Revolute_joint, accessed Jun. 10, 2025 (Year: 2025).*
International Search Report re PCT/CA2020/051236 mailed Nov. 26, 2020.
International Search Report re PCT/CA2020/051237 mailed Nov. 25, 2020.
Written Opinion re PCT/CA2020/051236 dated Nov. 26, 2020.
Written Opinion re PCT/CA2020/051237 mailed Nov. 25, 2020.
Chinese Search Report re Patent Application No. 2020800632325 dated Jul. 11, 2024 (original and English translation) (6 pages).
European Search Report re 20862069.0-1113 / 4013331 PCT/CA2020051237 dated Aug. 8, 2023 (12 pages).

* cited by examiner

HYBRID, DIRECT-CONTROL AND ROBOTIC-ASSISTED SURGICAL SYSTEM

CROSS-REFERENCE TO RELATED APPLICATION

This application is the U.S. 371 National Stage filing for PCT Application Ser. No. PCT/CA2020/051237, now published as WO 2021/046658, filed Mar. 6, 2017, which claims the benefit of U.S. provisional patent application No. 62/900,471 filed on Sep. 14, 2019, the entirety of each of which is hereby incorporated by reference.

FIELD OF THE INVENTION

In one of its aspects, the present invention relates to a hybrid, direct-control and robotic-assisted surgical system stabilizing apparatus that can be used to support at least part of the weight of a surgical device that is being used by a user/surgeon, so that at least some movements of the surgical device are manually driven by a user while at least some functions of the surgical device can be driven by a powered actuation unit.

INTRODUCTION

U.S. Pat. No. 10,639,066 (Vidal et al.) discloses a system for controlling displacement of an intervention device having an end for inserting in a patient body, including a base in a fixed position relative to the patient. A first portion has an arc member and is pivotally mounted on the base around a first axis (A1). A second portion includes a support member and a carrier member. The support member partially rotates around a second axis (A2). A third portion includes a holding member, and a sliding member mounted on the support member along a translation axis (AT). The holding member is arranged so that translation of the sliding member causes the intervention device to translate along a third axis (A3). The third axis (A3) is parallel to and offset from the translation axis (AT). When the carrier member is positioned halfway of the arc member, the first (A1), second (A2) and third (A3) axes are orthogonal.

U.S. Pat. No. 9,999,473 (Madhani et al.) discloses an articulated surgical instrument for enhancing the performance of minimally invasive surgical procedures. The instrument has a high degree of dexterity, low friction, low inertia and good force reflection. A unique cable and pulley drive system operates to reduce friction and enhance force reflection. A unique wrist mechanism operates to enhance surgical dexterity compared to standard laparoscopic instruments. The system is optimized to reduce the number of actuators required and thus produce a fully functional articulated surgical instrument of minimum size.

U.S. Patent Publication No. 2008/0091066 discloses an improved interface between the surgeon and an endoscope system for laparoscopic surgery, holding a laparoscopic camera and/or controlling an automated endoscope assistant includes at least one wireless transmitter with at least one operating key (12a). at least one wireless receiver (11), at least one conventional laparoscopy computerized system (15) loaded with conventional surgical instrument spatial location software, and conventional automated assistant maneuvering software, software loaded onto the conventional laparoscopy system that enables a visual response to the depression of at least one key on the wireless transmitter as well as an interface with the conventional automated assistant maneuvering software so as to achieve movement of the endoscope, and at least one video screen (30).

SUMMARY

Surgeries in the abdominal region (such as general surgery, gynecological operations, urology operations, and the like) are typically performed with either an open method, where a large incision is made to access the surgical site, or a minimally invasive surgery (MIS) method, where multiple smaller incisions are made, and slender instruments are used to manipulate tissue at the surgical site. MIS, also known as keyhole or laparoscopic surgery, offers numerous advantages to the patient, such as decreased blood loss, reduced scarring and reduced length of hospital stay. However, in many cases, the MIS approach is exceedingly difficult to perform, and the open method is implemented instead. A number of causes contribute to the challenges of MIS, but the main difficulties stem from the limitations of the surgical instruments and lack of adequate visualization. The surgical instruments often lack dexterity, making it difficult to perform fine tasks, such as suturing, in highly confined spaces.

Robotic-assisted surgery makes difficult MIS surgeries easier to perform by offering a number of advantages, including improved dexterity of the surgical instrument, improved visualization, motion scaling, and improved ergonomics. The use of robotics in surgery has steadily increased since 2000 when the da Vinci Surgical System (dVSS), by Intuitive Surgical, gained FDA approval. In 2018, the dVSS was used in over one million surgeries globally. Robotic-assisted surgical systems are ordinarily teleoperated, in which the surgeon sits at a master console and the surgeon's hand movements are replicated by one or more robotic arms which operate on the patient. Examples of other teleoperated robotic-assisted systems include products either in-development or commercially available, from companies such as CMR Surgical, TransEnterix, Titan Medical, and Medtronic.

The teleoperated robotic-assisted systems currently available have several drawbacks. Most significantly, many in the medical community claim there is insufficient clinical evidence to justify the cost of robotic-assisted surgery compared to traditional minimally invasive surgery; the capital cost of these robotic systems can exceed $2 million (USD), and cost anywhere from $2000-$6000 more per surgery compared to traditional laparoscopic surgery. Another major disadvantage is the lack of direct surgeon interaction with the patient, as the surgeon sits at a master console during the surgery, resulting in the loss of any natural haptic feedback and increasing the risk of injury due to errant instrument movements. Additionally, current surgical robotic systems are bulky, require expensive maintenance due to their complexity, and increase set-up time compared to traditional surgery resulting in longer surgeries.

The teachings herein describe a surgical system which aims to combine at least some of the key features of manual laparoscopic surgery and teleoperated robotic-assisted surgical systems. More particularly, the teachings herein related to a compact, counterbalanced remote-center-of-motion mechanism to which interchangeable surgical tools—such as wristed surgical instruments and/or endoscopes and the like—can be attached and provided with motorized actuation if desired. The system preferably allows the surgeon to manually position the attached surgical devices distal end/tip, while simultaneously providing robotic-assistance to control the device's end effector if desired, such as by driving a wristed end effector's orientation by replicating the surgeon's hand orientation on the grip portion of the system.

The teachings described herein may therefore provide one or more of the advantages of robotic-assisted surgery, such as, for example, relatively increased dexterity, with reduced technical complexity. This reduced complexity can be facilitated by reducing and/or eliminating the teleoperated approach. Instead, the robotic-assistance is integrated directly in a laparoscopic-like instrument, which is supported by a mechanism that can be attached directly to the operating table, or ceiling or cart mounted. By effectively integrating robotic-assistance directly into the surgical instrument, the complexity, cost, and setup time is reduced, while still providing natural force feedback.

In accordance with one broad aspect of the teachings described herein, a hybrid, direct-control and robotic-assisted surgical system for use with a surgical device having an elongate shaft extending from a distal tip comprising an end effector may include a stabilizing apparatus configured to at least partially support the weight of the surgical device and defining a remote centre of motion. The stabilizing apparatus may have a base member configured to be fixed relative to a patient and may include a device attachment unit that is movable relative to the base member and is configured to removably receive a surgical device having an elongate shaft and a distal tip. The stabilizing apparatus may be configured to constrain movement of the device attachment unit so that the device attachment unit and the distal tip are on opposite sides of the remote centre of motion and the elongate shaft intersects the remote centre of motion while the stabilizing apparatus is in use. A handle may be mechanically attached to the device attachment unit and may be configured to be grasped by a user whereby manual, Cartesian movement of the handle relative to the base member by the user results in corresponding Cartesian movement of the distal tip of the surgical device received in the device attachment unit. A robotic assist system may be configured to drive the end effector of the surgical device and may include: a sensor assembly configured to monitor at least a first attribute of the handle and generate a corresponding sensor signal; a controller communicably linked to the sensor assembly to receive the sensor signal and generate a corresponding primary control signal; and a powered actuation unit communicably linked to the controller to receive the primary control signal and configured to actuate an end effector of the surgical device received in the device attachment unit based on the primary control signal.

The stabilizing apparatus further may include: a hub rotatably connected to the base and rotatable about a rotation axis; an arcuate track connected to the hub and extending about a centre of curvature; and a linear translation apparatus connected to the arcuate track and movable relative to the hub so as to be pivotable about a pivot axis passing through the centre of curvature. The device attachment unit may be translatable along a translation axis relative to the arcuate track.

An intersection of the rotation axis, the pivot axis and a device axis that is parallel to the translation axis may define the remote centre of motion for the stabilizing apparatus. The device attachment unit may be configured so that when the surgical device is attached to the device attachment unit the elongate shaft extends along the device axis and intersects the remote centre of motion.

The linear translation apparatus may include a linear track extending from a fixed end connected to the arcuate track to a free end axially spaced apart from the fixed end, and wherein the device attachment unit is slidably connected to the linear track and translatable between the fixed and free ends.

A translation counterbalancing system may be configured to exert a biasing force on the device attachment unit to at least partially counterbalance a mass of the device attachment unit when the device attachment unit translates along the translation axis.

The arcuate track may be movably connected to the hub so as to be pivotable about the pivot axis. The linear translation apparatus may be non-movably connected to the arcuate track.

An arc counterbalancing system may include a biasing apparatus that is configured to exert a biasing force on the arcuate track to at least partially counterbalance a torque acting about the pivot axis.

The surgical device may be removable from the device attachment unit independently of the handle. The device attachment unit may be configured to removably receive a second surgical device.

The device attachment unit may be movable relative to the base member in response to a manual input from a user and without engaging a motor while the system is in use.

The handle may include a grip portion that is movable relative to the device attachment unit about at least a first degree of freedom. The first attribute may include the orientation of the grip about the first degree of freedom.

The grip may also be movable relative to the device attachment unit about a second and a third degree of freedom. The sensor assembly may be configured to monitor a second attribute, comprising the orientation of the grip about the second degree of freedom, and a third attribute, comprising the orientation of the grip about the third degree of freedom.

The handle may include a wristed grip portion that is movable relative to the device attachment unit about a pitch axis, a roll axis and a yaw axis. The sensor assembly may be configured to detect movement about each of the pitch, roll and yaw axes. The sensor signal may include a multi-channel signal. The primary control signal may include a corresponding multi-channel control signal. The powered actuation unit may be configured to cause corresponding movements of the end effector about an effector pitch axis, and effector roll axis and an effector yaw axes, whereby movements of the grip portion may be translated into corresponding movements of the end effector via the robotic assist system.

The powered actuation unit may include a plurality of rotatable actuation discs configured to interface with corresponding driving discs on the surgical device whereby the end effector can be driven about the effector pitch axis, effector roll axis and effector yaw axis.

The sensor assembly may include at least one potentiometer or encoder to detect the orientation/position of the grip about at least one of the pitch, roll and yaw axes.

The pitch axis, roll axis and yaw axis may intersect each other at a common point.

The handle further may include an auxiliary user input device that is communicably linked to the controller. The controller may be configured so that triggering the auxiliary user input device triggers a corresponding auxiliary action on the end effector.

The auxiliary user input device may include at least one of a switch, a button and a knob, and the auxiliary action on the end effector may include at least one of cauterizing, grasping, irrigating, and suctioning.

The translation counterbalancing system may include a counterweight that is translatable along the liner track and is operatively connected to the device attachment unit whereby translation of the device attachment unit causes an opposing translation of the counterweight to at least partially counterbalance the translation of the device attachment unit along the linear track.

The device attachment unit may be attached to a first side of the linear track and wherein the counterweight is attached to an opposing, second side of the linear track, and when the device attachment unit is translated in one direction the counterweight translates in an opposite direction, thereby counterbalancing the device attachment unit.

When the surgical device is attached to the device attachment unit a combined linear centre of mass of the linear track, the device attachment unit, the handle, the surgical device and the counterweight may be located at a reference position relative to the remote centre of motion. The combined linear centre of mass substantially remains in the reference position when the device attachment unit and the counterweight translated along the linear track.

A mass of the counterweight may be substantially equal to a combined mass of the device attachment unit, the handle and the surgical device.

A magnitude of the torque acting about the remote centre or motion may increase as an angular position of a first end of the accurate track relative to the hub changes from about 0 degrees to about 90 degrees, and the biasing apparatus may be configured so that a magnitude of the biasing force increases as the angular position of a first end of the accurate track relative to the hub changes from about 0 degrees to about 90 degrees.

The magnitude of the biasing force may remain substantially equal to the magnitude of the torque when the angular position of a first end of the accurate track relative to the hub is between about 0 degrees to about 90 degrees.

The device attachment unit may include the powered actuation unit, whereby the powered actuation unit is movable in unison with the device attachment unit relative to the base member.

The controller may be communicably linked to the sensor assembly using at least one of an electrical cable and a wireless communication protocol.

The device attachment unit may be configured so that when the surgical device is attached to the device attachment unit an axis of the elongate shaft is parallel to the translation axis.

The device attachment unit may be translatable along the linear track independently of the moving the arcuate track relative to the hub.

The hub, the arcuate track and the device attachment unit may be movable in response to a manual input from a user without engaging a motor.

The rotation axis may be substantially vertical when the base member is fixed.

A braking apparatus may be selectably engagable to inhibit movement device attachment unit about at least one of the rotation axis, the pivot axis and the translation axis.

The handle may be mechanically attached to the device attachment unit such that forces exerted on the distal tip of the surgical device received in the device attachment unit are transmitted to the handle thereby providing passive force feedback to the user grasping the handle.

The stabilizing apparatus may include: a hub rotatably connected to the base and rotatable about a rotation axis; a parallelogram structure connected to the hub; and a linear translation apparatus connected to a movable end of the parallelogram structure and movable relative to the hub with the moveable end of the parallelogram structure so as to be pivotable about a pivot axis, wherein the device attachment unit is translatable along a translation axis relative to the parallelogram structure.

A companion stabilizing apparatus may be configured to at least partially support the weight of a companion surgical device. The companion stabilizing apparatus may have a companion base member configured to be fixed relative to a patient and may include a companion device attachment unit that is movable relative to the companion base member and configured to removably receive a companion surgical device having an elongate shaft and a distal tip. The robotic assist system may also include a companion powered actuation unit communicably linked to the controller. The system may be selectably operable in a companion mode in which: the controller receives the sensor signal and generates a corresponding companion control signal; and the companion powered actuation unit may actuate the companion surgical device based on the companion control signal.

When the system is in the companion mode the controller may not generate the primary control signal whereby movements of the handle do not actuate the end effector of the surgical device received in the device attachment unit.

The companion stabilizing apparatus may be configured to define a second remote centre of motion and to constrain movement of the companion device attachment unit so that the companion device attachment unit and the distal tip of the companion surgical device are on opposite sides of the second remote centre of motion and the elongate shaft of the companion device may intersect the second remote centre of motion while the companion stabilizing apparatus is in use.

The companion base member may be spaced apart from the base member.

The companion surgical device may include an endoscope.

BRIEF DESCRIPTION OF THE DRAWINGS

Embodiments of the present disclosure will be described with reference to the accompanying drawings, wherein like reference numerals denote like parts, and in which.

DETAILED DESCRIPTION

Figure 1:
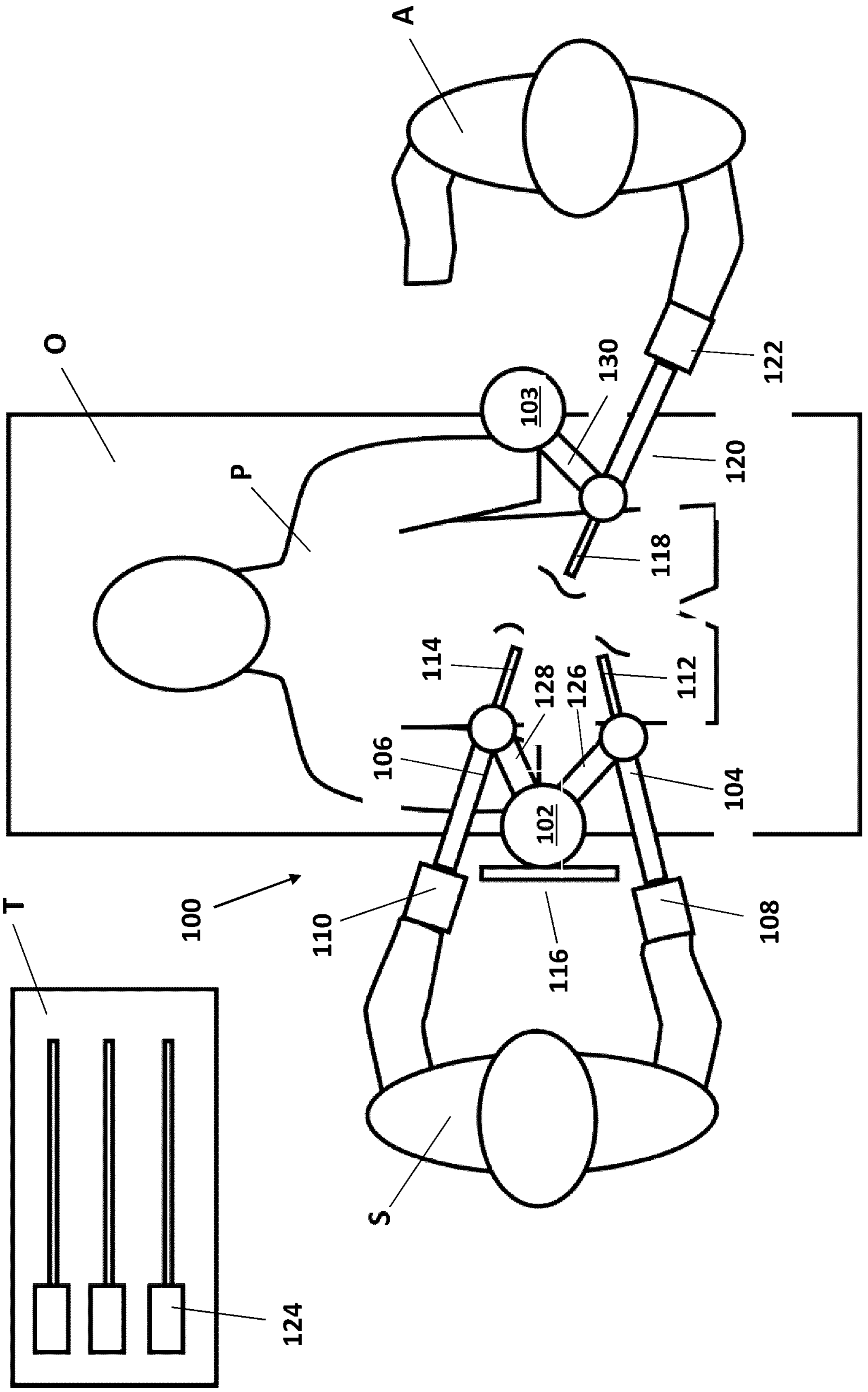
FIG. 1 is a schematic illustration of an overview of one example of a surgical system deployed in an operating room.

Various apparatuses or processes will be described below to provide an example of an embodiment of each claimed invention. No embodiment described below limits any claimed invention and any claimed invention may cover processes or apparatuses that differ from those described below. The claimed inventions are not limited to apparatuses or processes having all of the features of any one apparatus or process described below or to features common to multiple or all of the apparatuses described below. It is possible that an apparatus or process described below is not an embodiment of any claimed invention. Any invention disclosed in an apparatus or process described below that is not claimed in this document may be the subject matter of another protective instrument, for example, a continuing patent application, and the applicants, inventors, or owners do not intend to abandon, disclaim, or dedicate to the public any such invention by its disclosure in this document.

The teachings described herein relate, at least in part to a surgical system that includes a stabilizing apparatus with a device attachment unit that can receive one or more, preferably interchangeable surgical devices so that at least part of the weight of the surgical device is supported by the stabilizing apparatus while the surgical device is in use. The surgical devices used with the system may be any suitable type of devices, and may include surgical instruments having some type of active, actuatable end effectors (including those with wristed end effectors), surgical instruments with relatively simple or static end effectors (suction devices or retractors), endoscopes or other camera or vision systems and the like. Preferably, a common stabilizing apparatus can be used to support different types of surgical devices at different times. This may help facilitate the use, and preferably re-use, of 1, 2, or more relatively standardized stabilizing apparatus with a variety of different surgical devices at different times—such as using one stabilizing apparatus to support an endoscope and a second stabilizing apparatus to support a surgical instrument with a wristed end-effector in proximity to a single patient.

The stabilizing apparatus may be configured to allow movement of the supported surgical device about 1, 2, 3 or more degrees of freedom. This may allow the user to move the surgical device in generally the same way such a device could be moved without the use of the stabilizing apparatus. Preferably the stabilizing apparatus can also constrain the movement of the surgical device (when attached) to a predetermined range of motion in one or more of the relevant degrees of freedom such that it can permit movement of the surgical device about a remote centre-of-motion as described herein. This may help guide and/or constrain the movement of the distal tip of the attached surgical device within a pre-defined field of motion in addition to supporting at least some of its weight. That is, the configuration of joints in the stabilizing apparatus is preferably specifically configured to facilitate surgery by constraining the motion of the attached surgical device to a range of motion about a pivot point for minimally invasive access, also known as a remote-center-of-motion configuration. The surgeon may directly control the attached surgical device's end effector's position and orientation via any suitable user input apparatus, such as a multiple-degree-of-freedom (DOF) handle which is part of the unit in the examples described herein. The stabilizing apparatus is preferably configured so that the surgeon may control the position of the distal tip of the surgical instrument via the surgeon handle in substantially the same way they would control a manual instrument, with the overall motion device being preferentially constrained and supported by the remote-center-of-motion.

Preferably, the stabilizing apparatus will include one or more device attachment units that can be configured to detachably receive the surgical devices such that two or more different surgical devices can be used with the stabilizing apparatus. This may include using different types of surgical devices and/or using a new, sterile version of the same type of surgical device on subsequent surgeries. A used surgical device can be removed and optionally a different type of surgical device can be attached to the same device attachment unit without having to materially re-configure the stabilizing apparatus or device attachment unit itself.

Optionally, the surgical system may also include a robotic assist system that can be configured to drive, manipulate and otherwise actuate the end effector or other such actuatable feature on the surgical device. Preferably, the robotic assist unit can include a sensor assembly that is configured to monitor at least a first attribute or input from the user (such as the position of a handle, the triggering of a switch or button, a pressure applied to a pressure sensitive sensor and the like) using suitable sensors and to generate a corresponding sensor signal. The sensor signal can be provided to a suitable controller (that may be a computer, PLC, microprocessor, and the like) that can receive the sensor signal and generate a corresponding control or output signal that is appropriate for the specific surgical device that is in use. The output signal is provided to a suitable powered actuation unit that is communicably linked to the controller and is configured to drive the surgical device that is in use. That is, the powered actuation unit is configured to engage and drive the end effector of the surgical device based on the user inputs, and preferably to mimic the inputs from the user into corresponding actions/outputs by the end effector.

In some examples, the surgical devices used may be surgical instruments that have a wristed end-effector to allow for increased dexterity and can be attached or removed from the unit during the surgery as necessary depending on what type of instrument is required. The robotic-assisted unit is situated over the patient during the operation by a positioning arm.

Examples of the stabilizing apparatus unit may include a compact multi degree-of-freedom jointed mechanism which holds, stabilizes, and provides powered actuation for the attached surgical instrument's wristed end effector. The configuration of joints is preferably specialized for surgery by constraining the motion to a pivot point for minimally invasive access, also known as a remote-center-of-motion configuration. The surgeon directly controls the attached surgical instrument's end effector's position and orientation via a multiple-degree-of-freedom (DOF) handle which is part of the unit. The surgeon controls the position of the distal tip of the instrument via the surgeon handle just as they would control a manual instrument, with the motion constrained and supported by the remote-center-of-motion. A robotic-assisted actuation system integrated into the unit allows the surgeon to control the wrist of the surgical instrument's end-effector with natural hand motions captured by the multi-DOF surgeon handle.

With this configuration, the surgeon's hand motions are replicated by the wristed end-effector without the need for a master-slave teleoperated system; as such, the complexity and therefore the cost of the present surgical system can be less than master-slave teleoperated systems.

Optionally, the surgical system may also include a counterbalance system that can help counterbalance the weight/mass of the surgical device about 1, 2, 3, or more of the degrees of freedom of movement of the surgical device. As used herein, counterbalancing can be understood to mean offset at least a portion of the weight of the movable components of the surgical system to help reduce the load that is experienced by a user, or actuator, that is moving and/or manipulating the components of the surgical system. That is, if the moveable components of the system exert a torque about a given axis of rotation, or a linear force along a given axis of translation, then the surgical system can include a counterbalance system that is configured to exert a torque or linear force (for example) in an opposing direction, and having a pre-determined magnitude, to help reduce a net force that is acting on the movable components. The user, or actuator if applicable, need only then support the net force to hold the movable components stationary in a desired position. If the net force acting on the components is at, or substantially close to zero, then the movable components can be considered to be fully or about 100% counterbalanced, such that the net force exerted on the user is about zero and the movable components may remain practically stationary without intervention by the user.

The amount of degree of counterbalancing that a given example of the systems described herein may provide, about a given axis of motion) can be between about 0% of the forces exerted by the movable system components (e.g. the user feels the full weight of the components) and about 100% of the forces exerted by the movable system components (e.g. the user feels generally none of the weight of the movable components), and may be set a value between 0% and 100%. For example, the amount of counterbalance provided can be at least 10%, 20%, 30%, 40%, 50%, 60%, 70%, 80% and/or at least about 90% or more of the weight of the relevant movable system components. Preferably, the counterbalancing system can be configured to support at least 50% of the weight of the movable components (about a given joint/axis), and more preferably to support at least 75%, at least 85% or at least 90% of the weight of the movable components. Similarly, the amount of the weight of the movable system components that is borne by the user may be less than about 90%, 80%, 70%, 60%, 50%, 40%, 30%, 20% and/or about 10% of the total weight of the weight of the movable system components.

For example, the counterbalance system may be preferably configured so that the surgical device is substantially balanced when attached, such that the surgical device will remain generally in place in the absence of a force applied by the user. This may allow a device to positioned and then remain in position without the user continuing to hold the device, and it may then operate as a generally hands free device until the user grasps it again (such as to re-position). The counterbalance system may alternatively be configured to only counterbalance a portion of the weight of the surgical device. For example, in addition to surgical instruments, the system can be fitted to hold and stabilize an endoscope for advanced visualization.

The counterbalance system can optionally be configured as an entirely, or at least substantially passive system that can balance the movements of the medical devices using suitable springs, biasing members, cables, cams, gears and the like and without requiring motors, pneumatic or hydraulic systems or powered actuators or other active drive units. This may help simplify operation and maintenance of the stabilizing apparatus and may provide a desirable hand-feel experience for the user. It may also help reduce the need for fast acting sensors and drive calculations for any such motors, etc. Preferably, the forces exerted by the counterbalancing system can generally match the forces exerted by the surgical device so that if a user releases the handle and/or stops exerting a force on the system that the stabilizing apparatus and any devices supported thereon will remain in place. This may allow a user to release their grip, for example to rest his/her arm or reposition, while the surgical device remains substantially in the same position.

Alternatively, a counterbalancing system may include one or more powered actuation devices that can provide some or all of the desired counterbalancing forces. For example, the system can include one or more motors that can providing varying levels of torque while in use, such as having a system that can vary a given motor torque output based on the position of the movable components. The system may include servo-motors, suitable backdrivable motors and the like.

Optionally, a stabilizing apparatus that is considered passive for the purposes herein (e.g. without a driving mechanism to cause motion about one of its degrees of freedom) may include one or more braking devices that can help inhibit and optionally stop/lock movement about one or more of its degrees of freedom. Engaging such locking mechanisms may help ensure that the stabilizing apparatus and surgical device remain in a desired position/orientation even if the counterbalancing forces are not sufficiently equalized and/or of the apparatus is bumped or otherwise contacted when it is desired to keep it in a given location. The braking devices may include any suitable type of apparatus, such as latches, clutches, clips, pins, clamps, magnets and the like and may be manually triggered or may be remotely triggered using any suitable system, such as mechanical, electrical, hydraulic and pneumatic activation systems.

Optionally, one or more of the joints in the system can be sensorized to track its absolute or relative position, or both. Tracking the positions of the various joints in the system may help facilitate relatively precise tracking of position/orientation of the surgical device's distal tip for advanced functionality.

The systems described herein may also optionally provide the types of haptic feedback associated with traditional laparoscopic surgery, as the surgeon is directly manipulating the surgical instrument interacting with the surgical site and any resistance or forces that effect the position of the distal tip of the surgical device will be mechanically, and generally directly translated to the handle via the stabilizing apparatus to be experienced by the user.

A larger surgical system can include one or more stabilizing apparatuses, having device attachment units as described herein, each of which hold a surgical device, such as a surgical instrument. The surgical instruments preferably have a wristed end-effector to allow for increased dexterity and can be attached or removed from the stabilizing apparatus during the surgery as necessary depending on what type of instrument is required. The device attachment units may be held over the patient during the operation by stabilizing apparatuses. The surgeon may directly control each device attachment unit and attached instrument as they would a manual instrument. Some advantages of the described systems may include the ability to manipulate a dexterous wrist, having relatively improved ergonomics and reduced fatigue as compared to purely manual manipulation of an instrument (e.g. not supported by the stabilizing apparatus), while also providing similar level of fine motion control as compared to fully-robotic systems.

In addition to surgical instruments, the system can be fitted to hold and stabilize other devices such as an endoscope for advanced visualization. Each joint of the system can be sensorized, enabling precise tracking of the instrument tip for advanced functionality. The advantages of the described system include a dexterous wrist, improved ergonomics, and reduced fatigue compared to manual instruments, and a similar level of fine motion control compared to robotic systems. The invention also provides the haptic feedback associated with traditional laparoscopic surgery, as the surgeon is directly manipulating the surgical instrument interacting with the surgical site.

Optionally, the systems described herein may be configured to operate in both a primary mode and a companion mode, and may be selectably changeable between modes. In the primary mode, the user can engage the system handle and use it to be physically maneuver the movable components of the stabilizing system and to electronically/robotically drive or otherwise control the surgical device that is attached to the stabilizing system. In the companion mode, the system can also include a second, companion stabilizing system that can support and actuate a second, companion surgical device based on inputs a user provides using the same, primary system handle. In such examples, the control system for the surgical system, including the controller and handle-monitoring sensors, can be configured (for example via a switch, voice command or the like) such that the controller will receive the input signals from the sensors that related to the primary handle attributes but, preferably, instead of generating primary control signals to actuate the first/primary surgical device the controller will generate secondary/companion control signals that are communicated to a second/companion powered actuation unit that can then actuate the second/companion surgical device. This may allow a user to selctably control two different surgical devices, optionally on two separate stabilizing systems, using a common, physical handle.

Optionally, the companion stabilizing apparatus may be spaced apart from the primary stabilizing apparatus and can be movable independently of the primary stabilizing apparatus. The primary surgical device may include a wristed surgical instrument (having an articulating end effector) and the companion surgical device may be an endoscope that is spaced apart from the surgical instrument and supported by a separate companion stabilizing system. A surgeon may then use the primary handle to move and control the surgical instrument and its end effector and then to convert the system to its companion mode in which the same handle can then be used to reposition or otherwise adjust the operating parameters of the endoscope. With the endoscope reconfigured, the system can then be returned to its primary operating mode so that the handle can, once again, control the local surgical instrument.

Referring to FIG. 1, one example of a robotic assisted surgical system 100 is illustrated schematically as being within an operating room. In this example, a surgeon ("S") operates on the patient ("P") who is lying down on the operating table ("O"). This example of a robotic-assisted surgical system 100 has one example of a robotic surgical unit 104 with an example of a stabilizing apparatus that includes a support arm 102 that is attached to the side of the operating table O and which mechanically holds and supports the attached device attachment units. The surgeon S, standing or sitting, manipulates each robotic-assisted unit via integrated surgeon handles 108 and 110 to control the attached surgical devices which, in this example, include surgical instruments 112 and 114.

In this example, the surgeon views the surgical site via a live video on the monitor 116; the imaging is delivered via an endoscope camera 118, which in this example is also attached to a device attachment unit 120 supported by a second passive support arm 103 and can be manipulated by a surgical assistant ("A") via surgeon handle 122. In an alternative setup, the endoscope may be controlled by the surgeon, without the need for the surgical assistant. In other examples, the robotic-assisted unit to which the endoscope is attached may be programmed to automatically track the tips of the surgical instruments 108 and 110 to help maintain a desired view of the surgical site, optionally without human assistance.

The endoscope may be controlled using any suitable mechanism including, for example being controlled by the surgeon through one of the handles of a separate unit 108 or 110, or a foot-pedal, a handheld device, a glove-type device which translates the surgeons hand-movements into movements of the endoscope, voice-commands, or commands generated by a computer program, and the like. The surgeon may optionally view the endoscope image via a head-mounted unit instead of a monitor, or via a fixed stereoscopic viewing system. The image provided to the surgeon may be either 2D or 3D, the latter requiring a 3D image viewing method, such as stereoscopic goggles or a 3D viewing monitor and associated glasses.

The support arms 102, 103, in these examples each include a plurality of joints for positioning the attached device attachment units in the desired position and orientation for entry in the patient's abdomen wall (or elsewhere) to reach the surgical site. The device attachment units are each attached to respective linear translation apparatuses that include, in this example, support members 126, 128, 130 which extend from the passive support arm 102, 103. Once the device attachment unit is in the correct position for access to the surgical site, the support arm joints are optionally locked into place, either by mechanical or electronic brakes, to fix the entry point of the surgical instrument until released by the surgeon or surgical assistant.

Cartesian positioning of the attached surgical instrument's distal tip can be performed manually by the surgeon controlling the surgeon handle (such as handles 108 and 110) and is enabled by the joints of the stabilizing apparatus which are rigidly coupled to the surgeon handle 108 or 110. In examples where the joints and/or associated axes in the stabilizing apparatus are configured to constrain the entry point of the device attachment unit in a configuration known as a remote-center-of-motion (RCM).

The attached surgical instruments used in this example (such as instruments 112 or 114) preferably have a wristed end-effector at their tips with at least three degrees-of-freedom, such as pitch, yaw, and roll capabilities, and may preferably include grasping or some additional end-effector actuation, so that the surgeon S has increased manipulation at the surgical site compared to a non-wristed instrument. As it can be difficult to control multiple degrees-of-freedom of an end-effector mechanically, the device attachment unit preferably includes a powered actuation unit that is configured to control the orientation of the surgical instrument's wristed end-effector.

For example, to control the wristed instruments, the surgeon handle 108 or 110 may also have multiple-degrees-of-freedom, in the form of a joystick, gloves, a wristed handle, or the like, preferably so that the surgeon's hand movements are replicated or translated using a matrix transformation and/or mathematical operation to convert movement from the handle to the instrument tip end effector. The surgeon handle may also include, but is not limited to, other auxiliary or alternative control mechanism, such as a variety of buttons or knobs for more advanced functionality of the attached surgical instruments, such as the activation of suction, irrigation or cautery among others, or to control the position of the endoscope 118. The configuration described may allow the surgeon to control the instrument's wristed end-effector via replication of his or her hand movements captured by the surgeon handle; this control scheme is herein referred to as 'local teleoperation.'

As used herein, a remote-center-of-motion (RCM) is understood to refer to a configuration in which a series of joints or degrees of freedom pivot about a single point to which the mechanism (for example the stabilizing apparatus in this example) is not physically connected. The RCM can be used for minimally invasive surgical access, as it allows the surgical instrument to enter through a single point (herein referred to as the 'pivot point') into the body which remains fixed while allowing the surgical instrument to move within this constraint. This configuration may help prevent the surgical instrument from moving at the point at which it enters the patient's body (often the abdomen wall) and thereby helping to limit soft tissue damage at or around this location. An RCM may be achieved either through mechanical joints or software-imposed constraints. To achieve a software-imposed RCM, the joints are typically actuated or driven. While described with reference to one type of possibly surgery, the systems described herein may be used for surgery where minimally invasive access is feasible and need not be limited to surgeries currently being performed with a minimally invasive approach. Additionally, the systems may be used where the remote-center-of-motion is located outside of the patient, such as for transoral robotic surgery (TORS), for example.

The setup shown in FIG. 1 includes three robotic surgical units 104, 106 and 120, with two being used to hold for surgical instrumentation and one for the endoscopic camera. The number of device attachment units with attached surgical instruments used for an operation may vary based on a number of factors, including space constraints and the operation being performed, in addition to other factors. Space constraints may arise from the footprint of the stabilizing apparatus with respect to the operating table, and/or to avoid any collisions between device attachment units or instruments as they are used during an operation. In an alternative setup, the robotic surgical units 104, 106 and 120 may be mechanically supported in a desired position using any suitable base member that can be connected to the operating table (such as a pole or bracket), or the base member may include a patient-side cart on the operating room floor, a ceiling mount or other such mounting hardware. Depending on the surgical task, at any point during the operation the surgical instruments 112 and/or 114 may be removed from the corresponding robotic surgical unit 104 and/or 106 and replaced with a different surgical instrument 124 from the bedside tray ("T"), by the surgeon or surgeon assistant.

Figure 2:
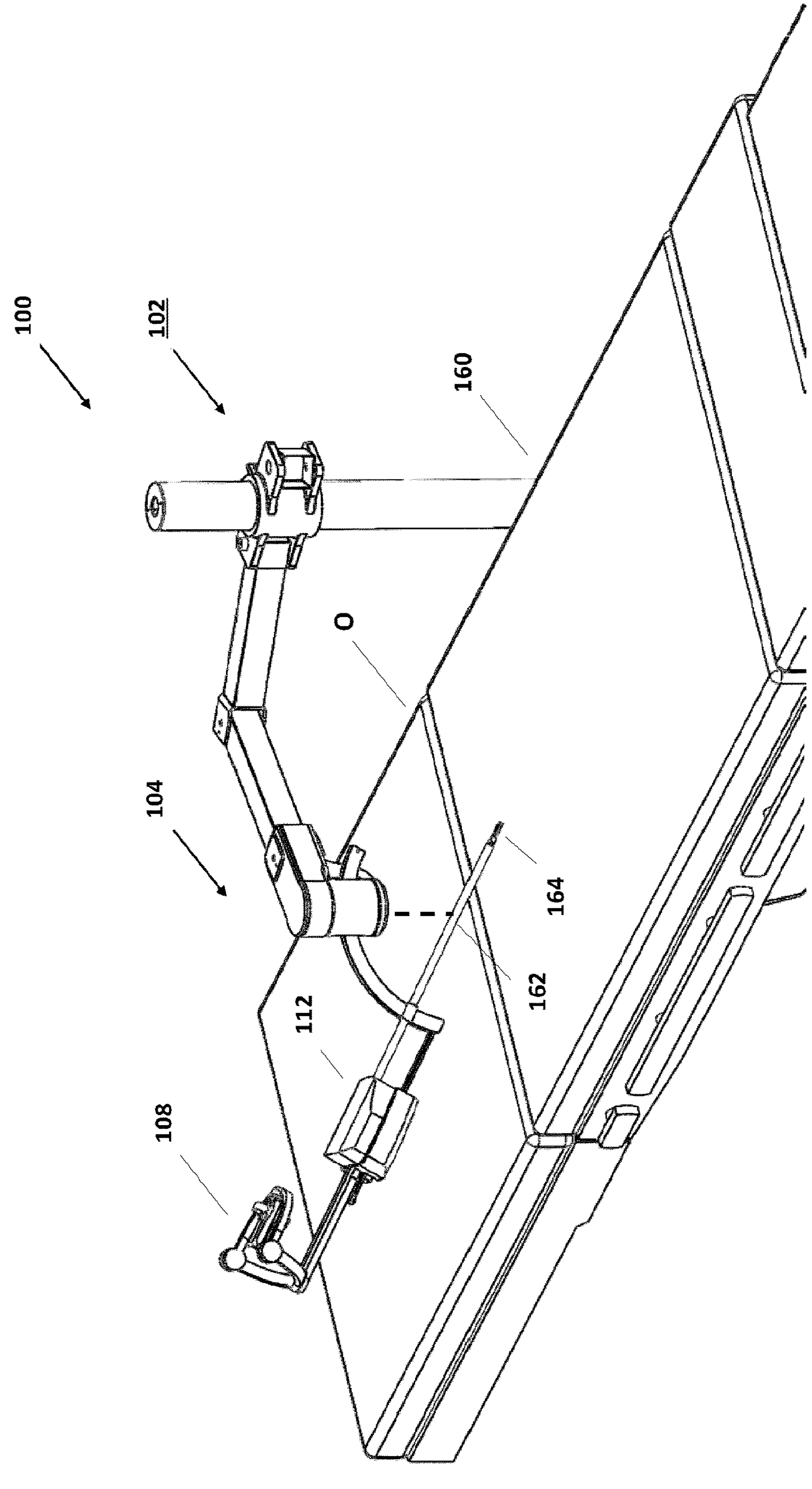
FIG. 2 is a perspective view of one example of a surgical system attached to a surgical table.

FIG. 2 shows a more detailed view of one preferred embodiment of a surgical system 100. In this example the stabilizing apparatus base includes a support arm 102 that is attached to the operating table at an attachment point 160. The robotic surgical unit 104 is attached to the support arm 102 and a surgical instrument 112 is removably attached to the robotic surgical unit 104. The robotic surgical unit 104 and its stabilizing apparatus in this example defines a mechanical remote-center-of-motion 162. The end-effector 164 of the surgical instrument 112 is manipulated by the surgeon via the surgeon handle 108. The attachment of the stabilizing apparatus to the surgical table may be achieved in a number of ways, such as a clamping mechanism, a bolting system, or the like. The operating table may be either manufactured with connection points or a connection method specifically for the attachment of the support arm 102, or the support arm may be designed such that it can be attached to any existing operating table.

Figure 3:
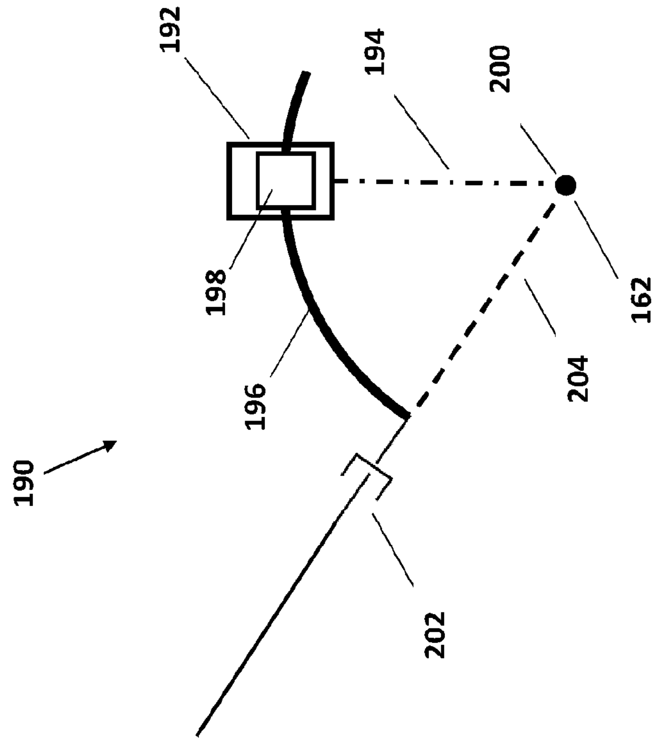
FIG. 3 is a schematic illustration of one example of a remote-center-of-motion (RCM) mechanism.

FIG. 3 shows the preferred configuration of joints 190 of the robotic surgical unit 104, used for positional control of an attached surgical instrument's end-effector, that includes a series of three joints which help enable and define the desired remote-center-of-motion. The mechanism is herein referred to as the "RCM mechanism". The first joint of the RCM mechanism is a hub that, in this example, includes a revolute joint 192 (herein referred to as the "revolute joint"), with rotation axis or axis of revolution 194. The second joint includes an arcuate track that extends about a centre of curvature and can be described as a remote revolute joint (herein referred to as the "arc joint") that, in this example, includes the arcuate track 196 which can move relative to a motion carriage 198 fixed in hub 192 which creates a remote axis of rotation or pivot axis 200 that passes through the centre of curvature of the arcuate track 196. The remote axis of rotation 200 perpendicularly intersects the axis 194 of the first revolute joint 192. The third and final joint of this example of an RCM mechanism includes a linear translation apparatus having a prismatic joint 202 (herein referred to as the "prismatic joint") that is affixed to the arcuate track 196. The prismatic joint 202 is arranged such that its axis of translation 204 passes through the intersection point of axis 194 and axis 200. The combined intersection of each joint axis defines the remote-center-of-motion 162. The configuration of joints described above may facilitate an attached surgical instrument to be inserted into the patient's body for minimally invasive access.

Figure 4:
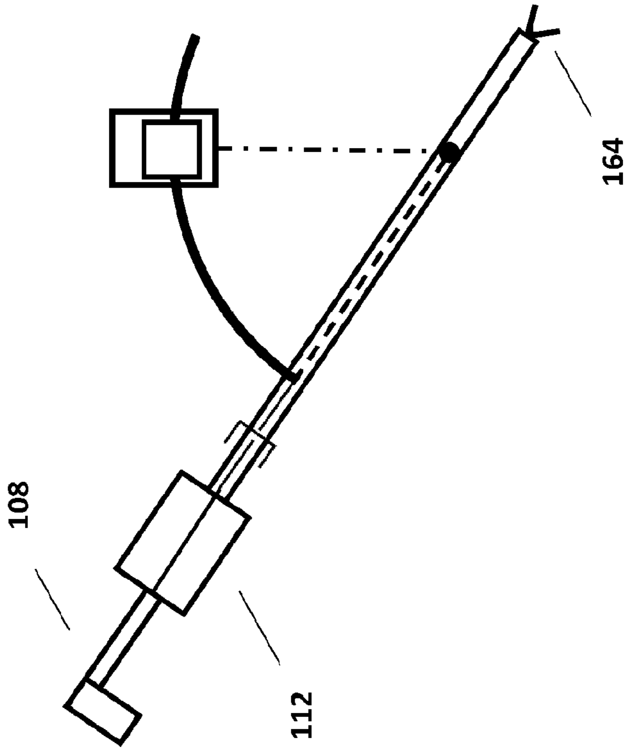
FIG. 4 is a schematic illustration of the RCM mechanism of FIG. 3 with surgical instrument attached.

In the preferred embodiment, the revolute joint in the hub is the first joint in the series of joints which create the RCM mechanism, followed by the arc and prismatic joint. In the preferred embodiment, the revolute joint is configured as illustrated in the present figures so that the rotation axis is at least substantially vertical when the system 100 is in use, i.e. that the rotation axis is perpendicular to the floor. In other embodiments, the arrangements of the revolute, arc, and prismatic joints may be altered to achieve the same or similar RCM motion. For example, the revolute joint may be moved to a lateral position, with its axis of revolution parallel to the floor. In another instance, the arcuate track 196 is fixed to the hub 192, while the carriage 198 containing rolling elements can move along the arcuate track 196. In this example, the prismatic joint 202 is fixed to the movable carriage 198 to maintain a remote center of motion. FIG. 4 shows the same RCM mechanism 190 with an attached surgical instrument 112. The surgical instrument 112 is attached to the prismatic joint, the last of the three joints that comprise the RCM mechanism. The surgeon manipulates the end-effector 164 of the surgical instrument 112 via the surgeon handle 108.

Figure 5:
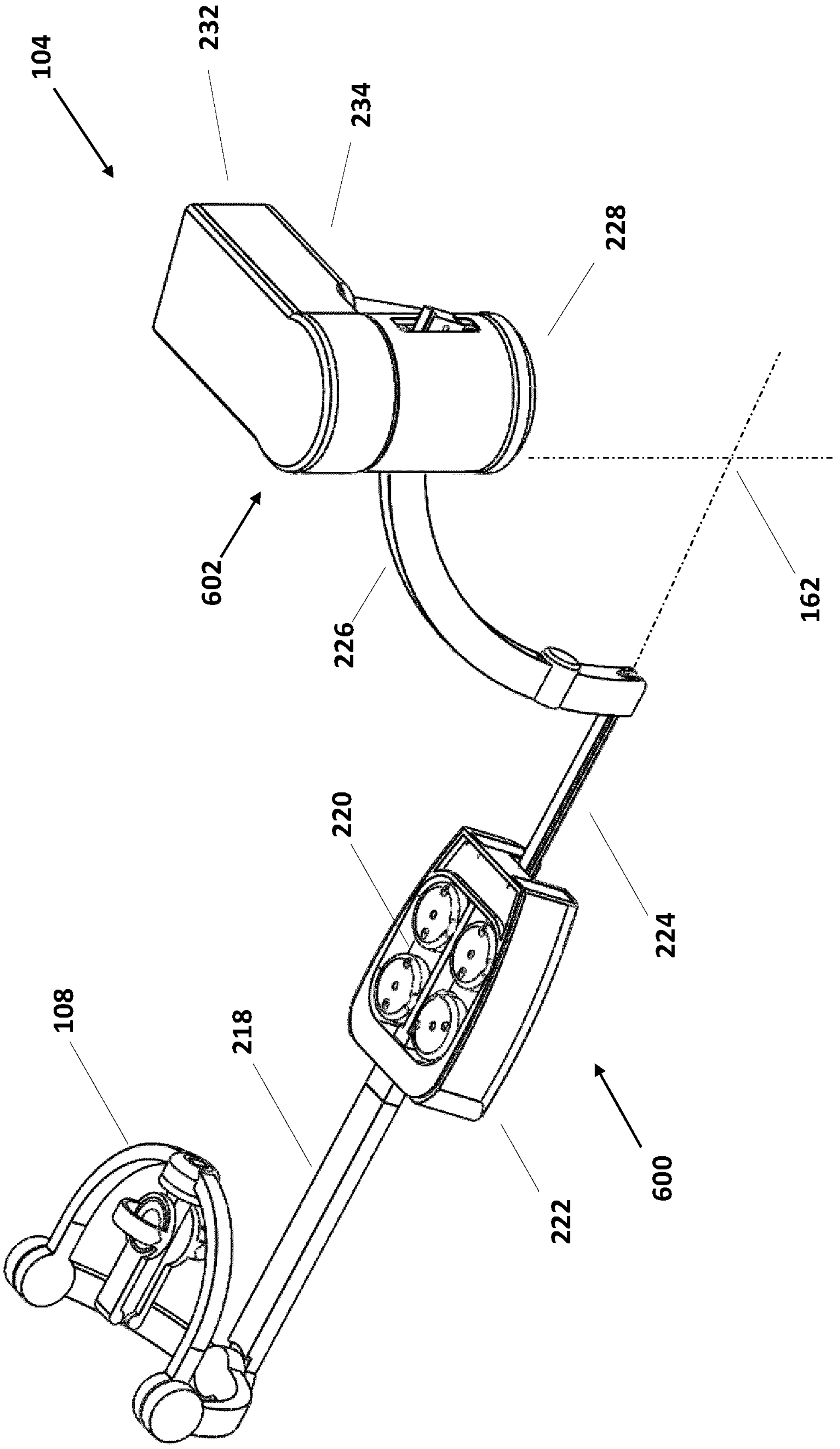
FIG. 5 is a front perspective view of a portion of the surgical system of FIG. 2.

FIG. 5 shows one preferred embodiment of the robotic surgical unit 104, including all robotic-assisted components and the RCM mechanism, with the surgical instrument removed from the image for clarity. Referring also to FIG. 2, this embodiment includes a remote-center-of-motion 162, a surgeon handle 108, a handle connector 218, a device attachment unit including an instrument interface 220 and an actuation unit 222, a linear translation apparatus including a prismatic track 224, an arcuate track 226, a hub that includes a revolute joint 228, and a base member that includes a connection plate 232 and a base 234 for securing to the support arm 102. This system also includes a translation counterbalance system in the form of a prismatic counterbalancing system 600, and an arc counterbalancing system in the form of a spring-cam counterbalancing system 602.

In this example, the surgeon can control the robotic surgical unit via the surgeon handle 108. In this preferred embodiment, the surgeon handle 108 consists of a joystick-like device with multiple-degrees-of-freedom for robotically manipulating the wristed end-effector of the surgical instrument. The surgeon handle contains multiple sensors to read the current orientation of the surgeon handle 108. The surgeon handle 108 is rigidly attached to the actuation unit 222 via a handle connector 218, which is hollow and carries multiple electrical wires running between the sensors in the surgeon handle and the actuation unit. The actuation unit 222 houses motors, motor drivers, motor encoders, and a microcontroller for control and actuation of the attached surgical instrument's end-effector. The instrument interface 220 is a mechanism to which the surgical instrument is attached and provided with rotary motion for actuation of the surgical instrument's end-effector and is part of the same component as the actuation unit 222. The surgical instrument is designed to easily attach to, engage with, and subsequently release from the instrument interface.

In this example the actuation unit 222 and the prismatic track 224 each are part of the prismatic joint of the RCM mechanism. The prismatic track 224 is a linear track or rail member that extends between its first end that is preferably rigidly attached to the arcuate track 226 and an opposing free, second linear track end. The track 224 is preferably at least substantially linear such that axes that are parallel to the translation axis defined by the linear track will intersect the other axes as desired to help define the RCM point. Slight deviations from a perfectly linear track that do not misalign the axes or interfere with the RCM point functionality can still be considered substantially linear for the purposes of the present teachings.

The arcuate track 226 passes through the revolute joint 228 in the hub to form the arc joint of this example of the stabilizing apparatus. A mounting plate 232 is located at the rear of base 234 for attachment to the support arm 102. The spring-mass counterbalancing system 602 is housed within base 234, and the prismatic counterbalancing system 600 is located along the prismatic track 224.

Figure 6:
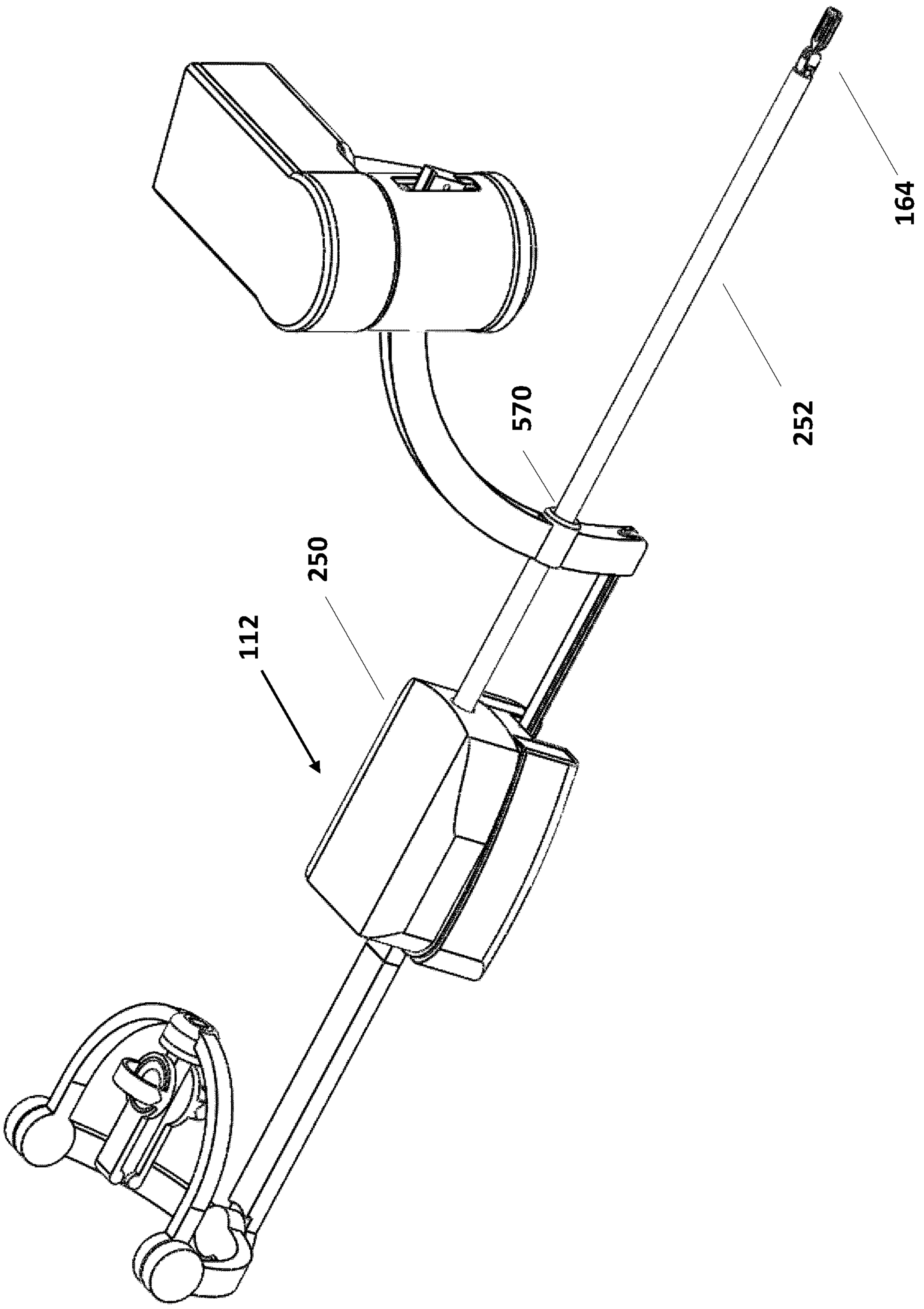
FIG. 6 is the front perspective view of a portion of the surgical system of FIG. 5 with a surgical instrument attached.
Figure 6A:
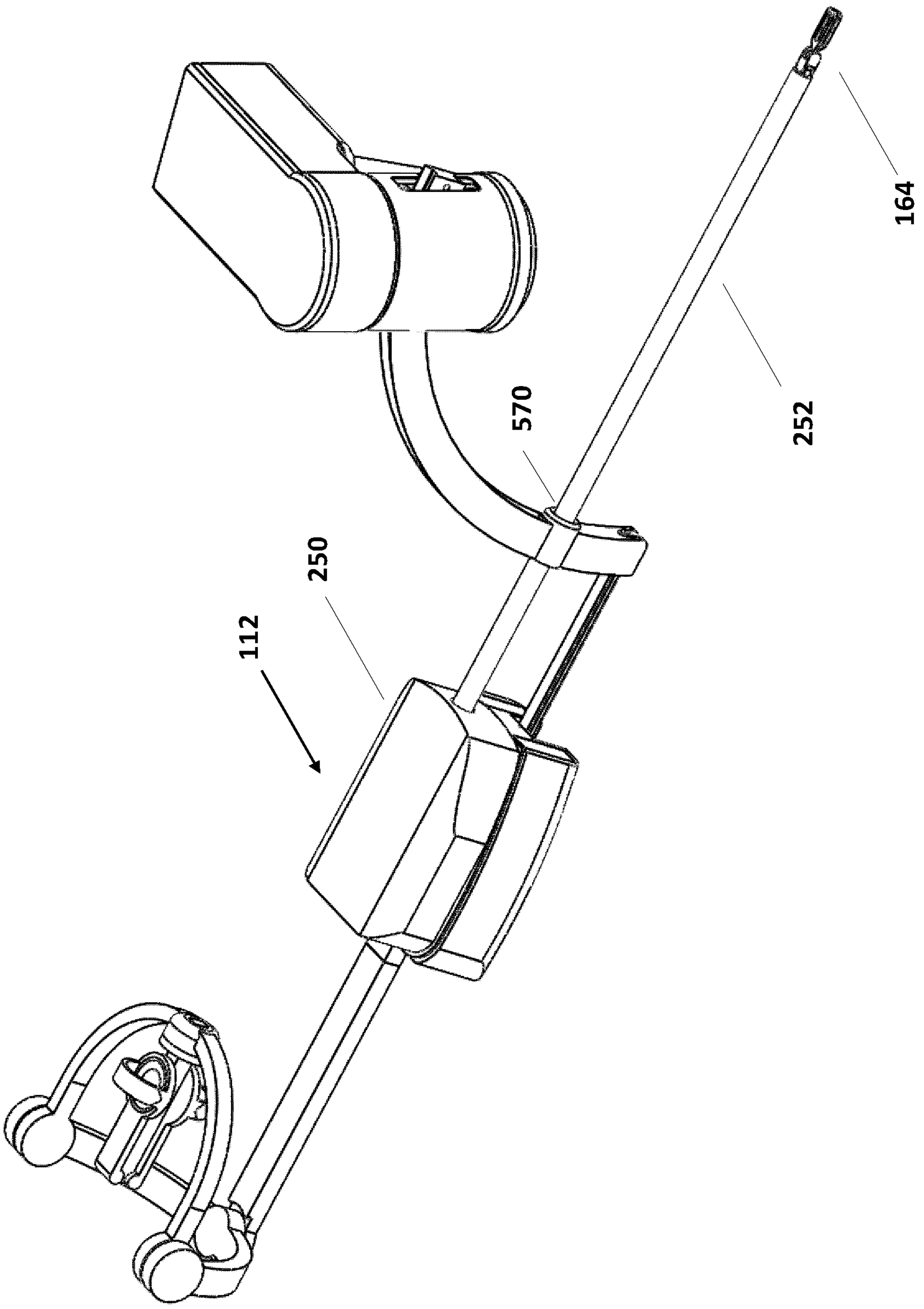

FIG. 6 shows the surgical system with a surgical instrument 112 connected to its device attachment unit. In this example the surgical instrument 112 includes a surgical instrument base 250, an elongate shaft 252 that extends along a shaft axis between the base 250 and a distal tip, and an end effector 164 provided at the distal tip. In this example, the surgical instrument has at least 3 degrees-of-freedom at the end-effector in a wristed configuration, plus a fourth degree of freedom for actuation of graspers, scissors, or the like. The end-effector 164 may be driven by any number of methods such as cables, pushrods, fluidic actuation, or the like, to translate the motion at the instrument base 250 down the elongate shaft 252 to the end-effector 164. The mechanically wristed end-effector may be achieved by multiple methods such as gears, pulleys, flexural joints, or the like. The stabilizing apparatus may include other device attaching and stabilizing features, which may help support, orient and align the surgical device. In this example the arcuate track 226 includes a device aperture 570 that is sized to accommodate the elongate shaft 252 of the surgical instrument. A cannula may be fitted into the device aperture 570 and secured via press-fit and can help guide the surgical instrument as it is being connected to the stabilizing apparatus. The cannula can also provide an access point for minimally invasive operations. The cannula may be disposable and differently sized cannulas can be used depending on the instrument used during the operation, for example, to fit standard surgical instrument shafts diameters of either 5 mm or 8 mm.

Figure 7:
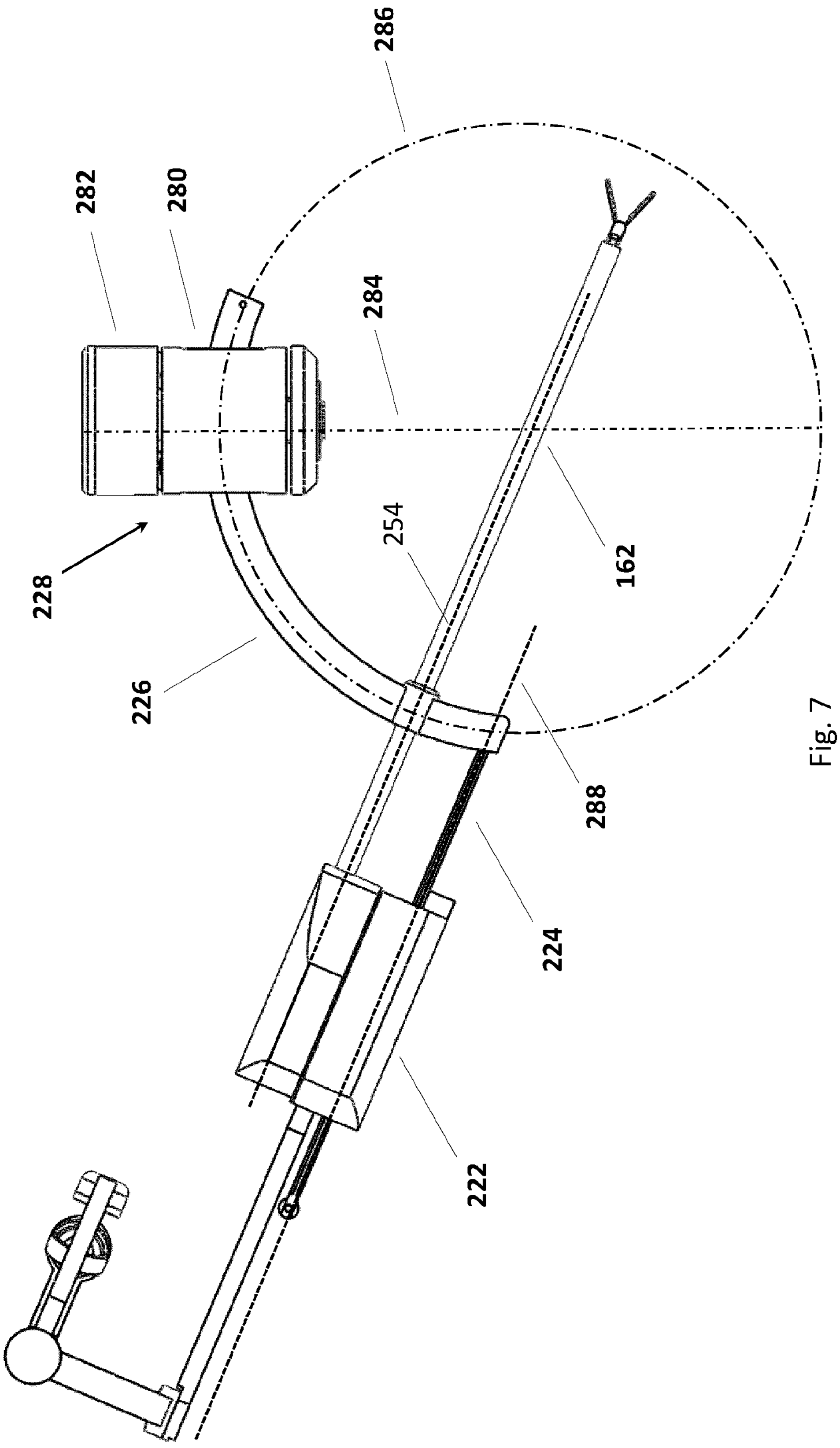
FIG. 7 is a side view of a portion of the surgical system with a surgical instrument attached.

Referring also to FIG. 7 the revolute joint 228 in the hub is the first joint in the series of three joints that comprise the RCM mechanism, and consists of a clevis-style inner revolute 280 and outer revolute 282. The outer revolute 282 supports the inner revolute 280 at both the top and bottom of the joint. The inner revolute 280 is free to rotate about axis 284 while the outer revolute 282 is fixed. The second joint is a remote revolute joint formed by the arcuate track, also known as the arc joint, which rotates about the remote-center-of-motion 162. This arc joint includes the arcuate track 226 and rolling elements contained within the inner revolute 280. The arcuate track 226, and subsequent attached components including the prismatic track 224 and actuation unit 222, revolves around the remote-center-of-motion 162 with an arc diameter indicated by the arc/circle 286. The prismatic joint includes the device attachment unit having its powered actuation unit 222 that is configured to include linear translation elements that can engage the linear track 224 so that the device attachment unit can move/translate along the stationary prismatic track 224 which is fixed to the arcuate track 226. When the instrument is attached, the shaft axis 254 defined by the elongate shaft 252 is parallel to the translation axis 288 of the linear track 224 and intersects the remote-center-of-motion 162 to complete the 3-degree-of-freedom remote-center-of-motion mechanism.

In other embodiments, there may be alternative mechanical methods of achieving the motion produced by each joint while maintaining the same overall joint configuration. For example, the revolute joint may be achieved without a clevis joint design, where the outer revolute 280 attaches to the inner revolute 282 at only the top or bottom of the joint. In another embodiment the arc joint may be achieved with a fixed arcuate track 226 and rolling elements contained at the distal end of prismatic track 224 to allow it to travel along the arcuate track 226. In another embodiment, the arc joint may be achieved by a telescoping joint design, eliminating the need for roller elements contained within the inner revolute joint 280. For example, the telescoping arc joint could consist of several links which collapse and extend with respect to each other to create the desired remote revolute motion. Similarly, the prismatic joint could be achieved by including rolling elements on the arcuate track 226 and allow the entire prismatic track 224 to translate along axis 288. In this example, the rolling elements in the actuation unit 222 would be removed and instead the actuation unit would be rigidly fixed to the prismatic track 224. In another example, the prismatic track could be achieved with a telescoping method as described above for the arc joint. An advantage of the telescoping joint design is the elimination of components which remain fixed in size, such as the arcuate track 226 and prismatic track 224.

In this embodiment, the stabilizing apparatus is purely passive and used as a positioning system for the end-effector 164 of the attached surgical instrument 112. In another embodiment, each joint of the RCM mechanism may contain sensors, such as a potentiometer or encoder, to continuously record joint data. As the RCM mechanism is a three degree-of-freedom system, an analytical kinematic model exists for such systems, and the position of the end-effector 164 can be calculated by a suitable controller using joint data captured by such sensors. The position of the instrument's end-effector 164 can be used in a multitude of ways, such as for intra-operative instrument navigation and tracking, recording of all instrument data during operations, or for surgical education purposes. For example, the economy of motion of the surgical tip (i.e. path length) or jerk (derivative of acceleration) can be analyzed in real-time or post-operatively to determine surgeon skill and/or surgical outcomes.

In optional alternative embodiments, any or all of the three RCM joints may include suitable braking apparatuses, such as electronically or mechanically controlled brakes, for additional functionality, such as the ability to actively dampen any or all joints for finer motion control, virtual fixtures to prevent damage to tissue away from the surgical site, or the ability to lock one or more joints during a given surgical task. The ability to selectably lock and unlock one or more joints could, for example, allow the surgeon to hold tissue in a specific position or enable the RCM mechanism to hold its exact position during an instrument exchange. The advanced functionality discussed above, such as joint dampening, joint locking, or virtual fixtures, could be controlled by the surgeon in a plurality of methods, for example, via buttons, switches, knobs or the like include on the surgical handle, on a touchscreen located near the surgeon's reach, or via foot pedal. In an alternative embodiment, the advanced functionality could be activated by the surgical assistant. In an alternative embodiment, any or all of the RCM joints may be motorized through the inclusion of an actuator, such as a motor, either integrated into each joint for direct drive or located away from the joint and driven via a transmission system, for example using a cable or belt or geared system. The motorization of the RCM mechanism, in conjunction with sensorization (i.e. adding sensors to each joint), would allow for more advanced functionality, such as active haptic feedback, full teleoperation (the surgeon controls the robotic unit via a console), or semi-autonomous or fully autonomous surgical tasks.

Figure 8:
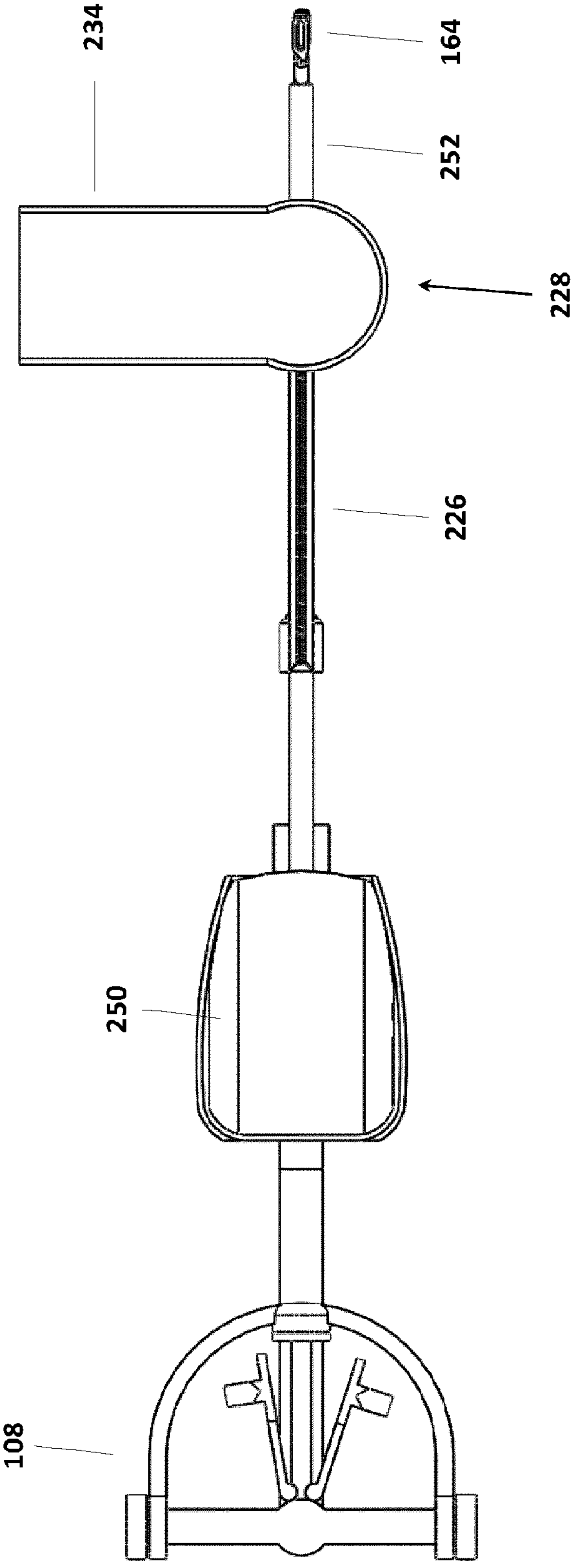
FIG. 8 is a top view of the surgical system.
Figure 10:
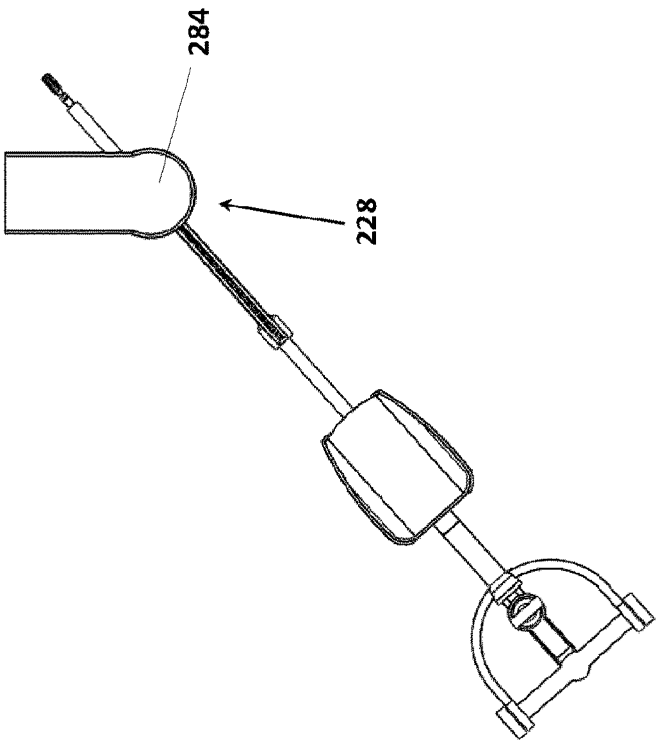
FIGS. 9-10 are top views showing one example of a range of motion of about a hub of the surgical system.
Figure 9:
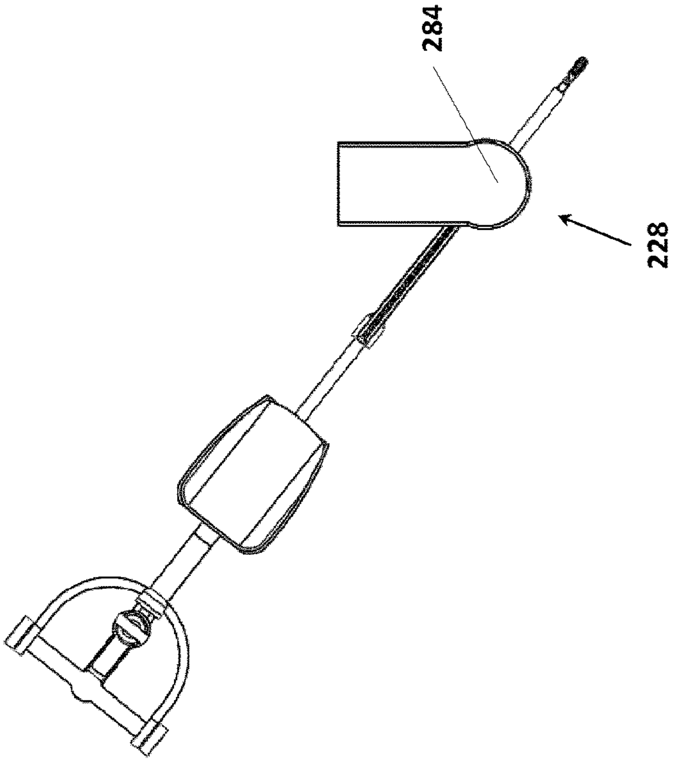

When the stabilizing apparatus is used the hub can permit rotation of the arcuate track, linear translation apparatus and device attachment unit mounted thereto about the rotation axis 284 within a pre-determined range of motion. This range of motion can be limited, using any suitable stops or other such hardware or software limits, to any suitable range of motion, including about 45 degrees or less, about 90 degrees or less, about 180 degrees or less, about 270 degrees or less and/or about 360 degrees. This may help limit the field of movement of the surgical device to within a desired field of use and may help prevent collisions between the surgical device and other objects in the operating theatre. Alternatively, the hub can permit free rotation about the rotation axis 284 for a full 360 degrees and beyond which may help provide a generally unrestricted range of rotational motion for the use. For example, FIG. 8 shows a top view of the robotic surgical unit with an attached surgical instrument in a first rotational position, while FIG. 9 and FIG. 10 illustrate examples of how portions of the stabilizing apparatus can be rotated about the hub/revolute joint 228 of the RCM mechanism and rotation axis 284.

Figure 12:
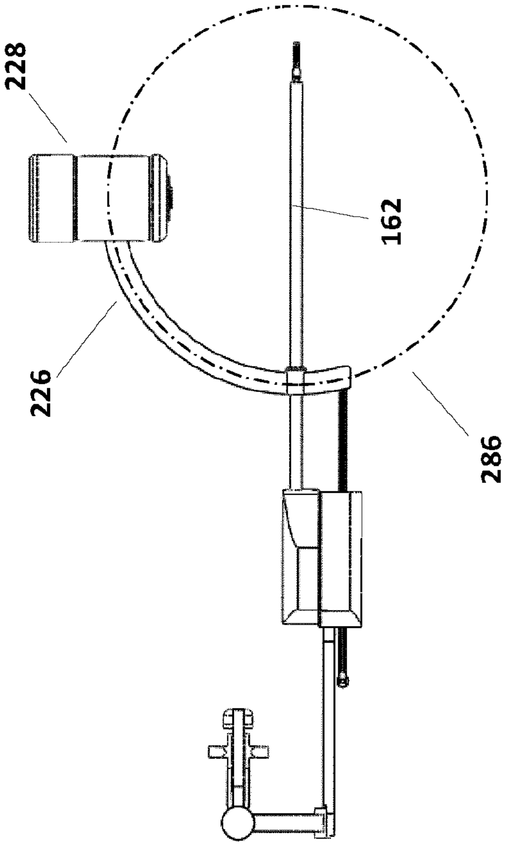
FIGS. 11-12 are side views showing one example of a range of motion of one example of an arcuate track of the surgical system.
Figure 11:
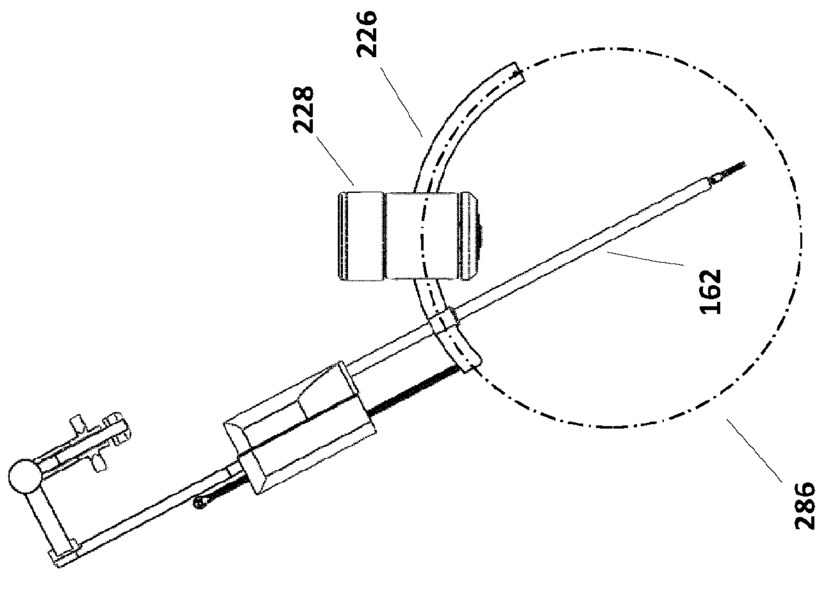

Similarly, the revolute joint 228 and arcuate track 226 are, in this illustrative example, configured to permit movement of the arcuate track 226 along its path of curvature/arc circle 286 (and about the pivot axis 200/remote pivot 162) through a desired range of motion. In the present example, the range of motion of the arcuate track 226 (and the other components mounted thereon) is generally limited by the physical extent/configuration of the track 226, as it can generally move along its length and between is respective arcuate track ends. In the illustrated example the arcuate track 226 has an arc length (e.g. subtends and angle of) about 45 degrees, but in other examples may have shorter or longer arc lengths—which could then provide smaller or larger ranges of movement/travel about the pivot axis 200. For example, FIG. 11 and FIG. 12 show how the arc joint motion is achieved along the arc circle 286 and rotation about the remote-center-of-motion 162 for the present example. In FIG. 11 the arcuate track 226 is positioned near a first limit position, in which the end of the arcuate track 226 that is connected to the linear translation apparatus is adjacent the hub, and FIG. 12 shows an opposing arcuate position in which the opposing, second end of the arcuate track is adjacent the hub and the end of the arcuate track 226 that is connected to the linear translation apparatus is spaced apart from the hub. In the illustrated examples, the movement of the arcuate track 226 is independent of the rotation of the hub about the rotation axis 284.

Figure 14:
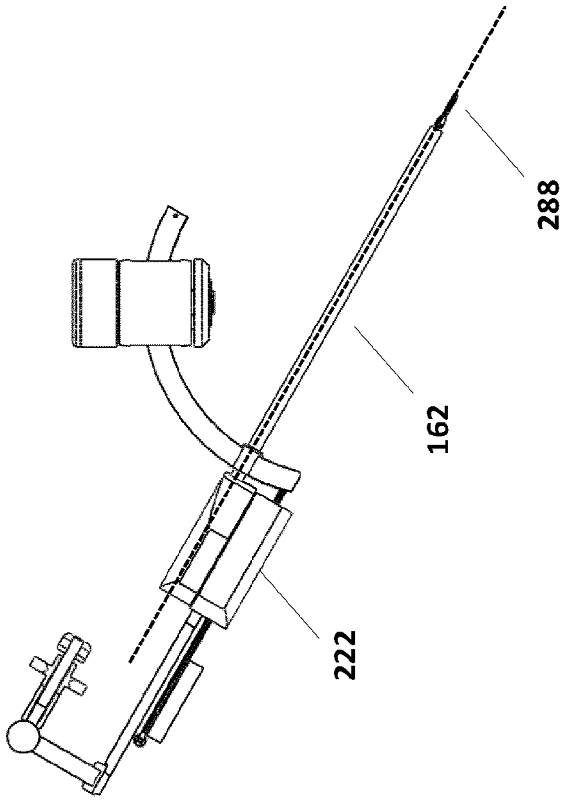
FIGS. 13-14 are side views showing one example of a range of motion of the translation apparatus of the surgical system.
Figure 13:
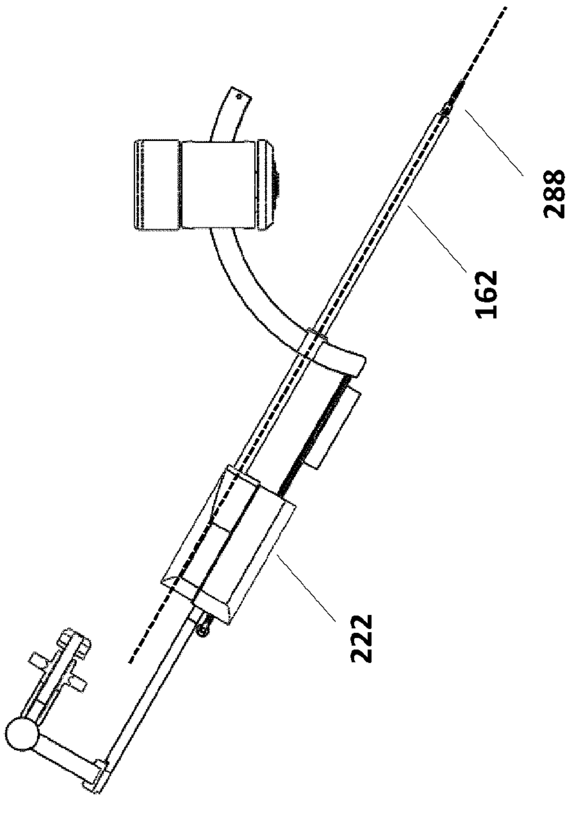

The stabilizing apparatus is also preferably configured so that translation along the linear translation axis, e.g. axis 288 in this example, can occur independently of rotation above axis 284 or pivoting about the pivot axis 200. Like the movement of the arcuate track 226, in the illustrated example the extend of translation of the device attachment unit is generally limited to the physical length/extent of the linear track 224 as the device attachment unit can slide along the track 224 between its opposing fixed and free ends. For example, FIG. 13 and FIG. 14 show movement of the device attachment unit relative to the rest of the stabilizing apparatus along translational axis 288, with FIG. 13 showing the actuation unit 222 in an outboard or retracted position (in which the actuation unit 222 is at the free end of the track 224), and FIG. 14 showing the actuation unit 222 in an inboard or extended position (in which the actuation unit 222 is at the fixed end of the track 224, adjacent the arcuate track 226).

Figure 16:
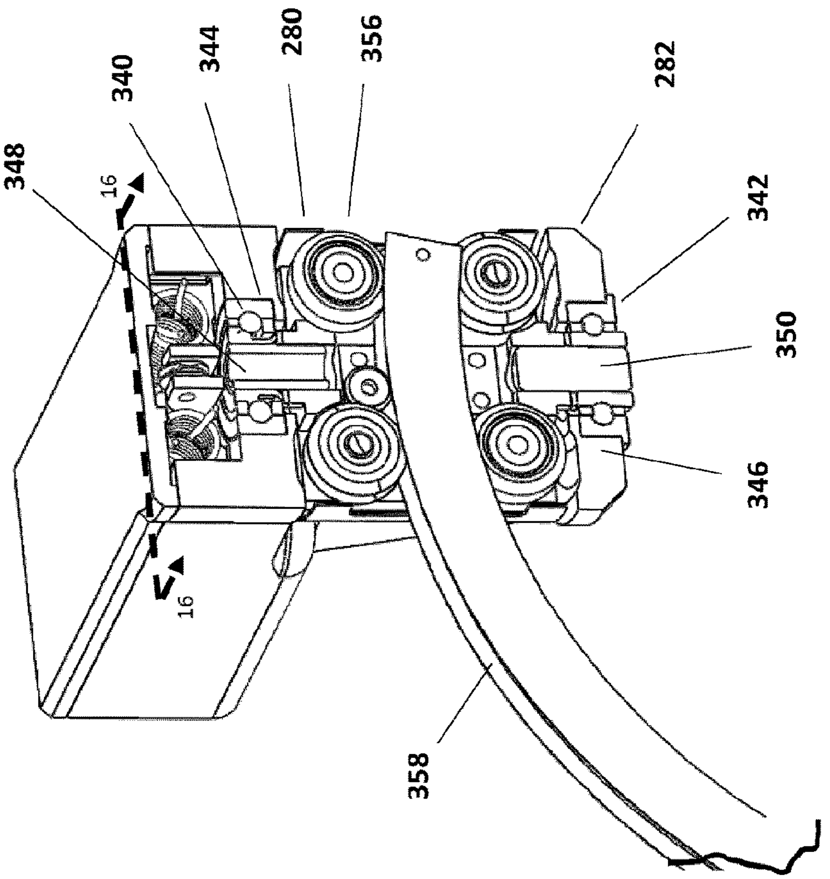
FIG. 16 is a cross-sectional, perspective view of the portion of the surgical system shown in FIG. 15, taken along line 16-16.
Figure 15:
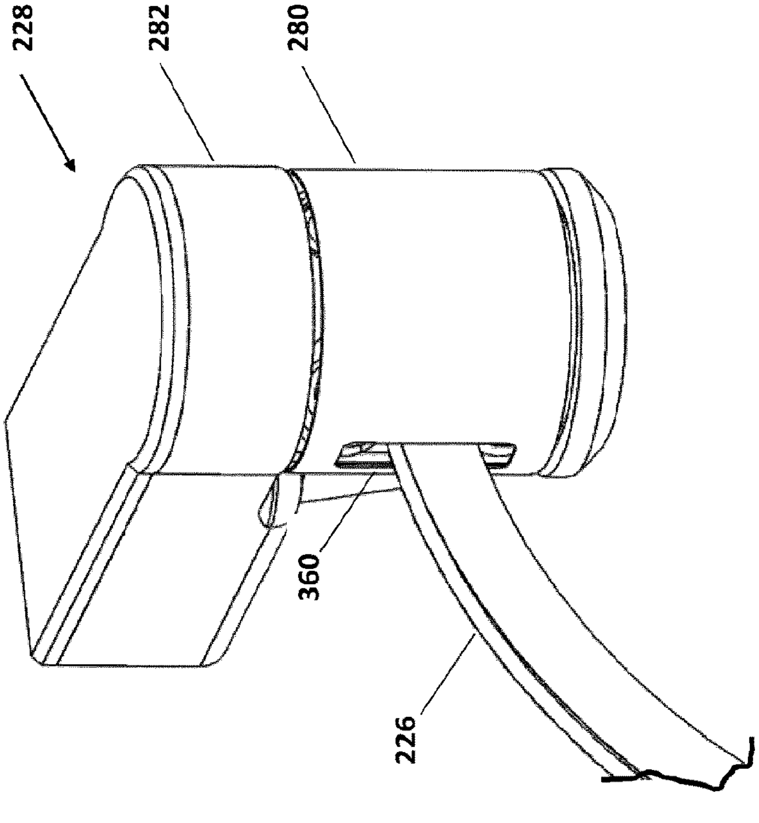
FIG. 15 is an enlarged view of a portion of the surgical system.

The hub that is used in the stabilizing apparatus may include any suitable hardware that can support the arcuate track and other system components while still permitting the desired rotation about the hub's rotation axis. In the present example, the hub includes the revolute joint 228 which is illustrated in more detail in FIGS. 15-16. With reference to FIGS. 15 and 16, in this example the revolute joint 228 is a clevis arrangement including of an inner revolute 280, which is able to rotate, and an outer revolute joint 282, which is fixed. Flanged bearings 340 and 342 are press-fit into the bearing housing 344 and 346 which are part of the outer revolute 282. D-profile shafts 348 and 350 pass through the flanged bearings 340 and 342 and are press-fit into corresponding housings of the inner revolute 280. All shafts and bearings are secured with set-screws. The inner revolute 280 contains four v-groove rollers 356 which mate with the 90-degree track profile 358 of arcuate track 226, allowing the arcuate track 226 to move. A cut-out 360 in the wall of the inner revolute joint 280 allows the arcuate track 226 to pass through the exact center, aligning the axes of the revolute and arc joints. The clevis arrangement shown limits the revolute joints range of motion to approximately 270 degrees. An alternative embodiment may eliminate this reduced range of motion by, for example, eliminating the bottom of the clevis joint.

Figure 17:
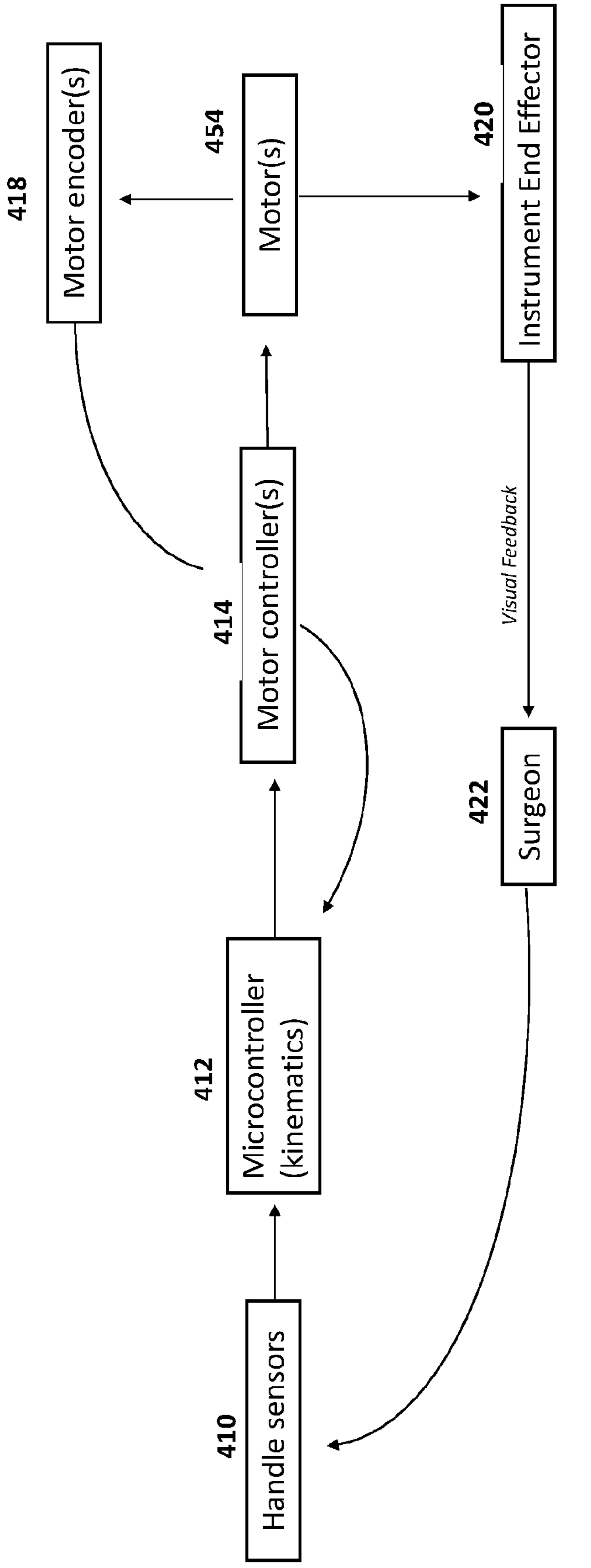
FIG. 17 is a flow chart illustrating one example of a localized teleoperation control schematic.
Figure 18A:
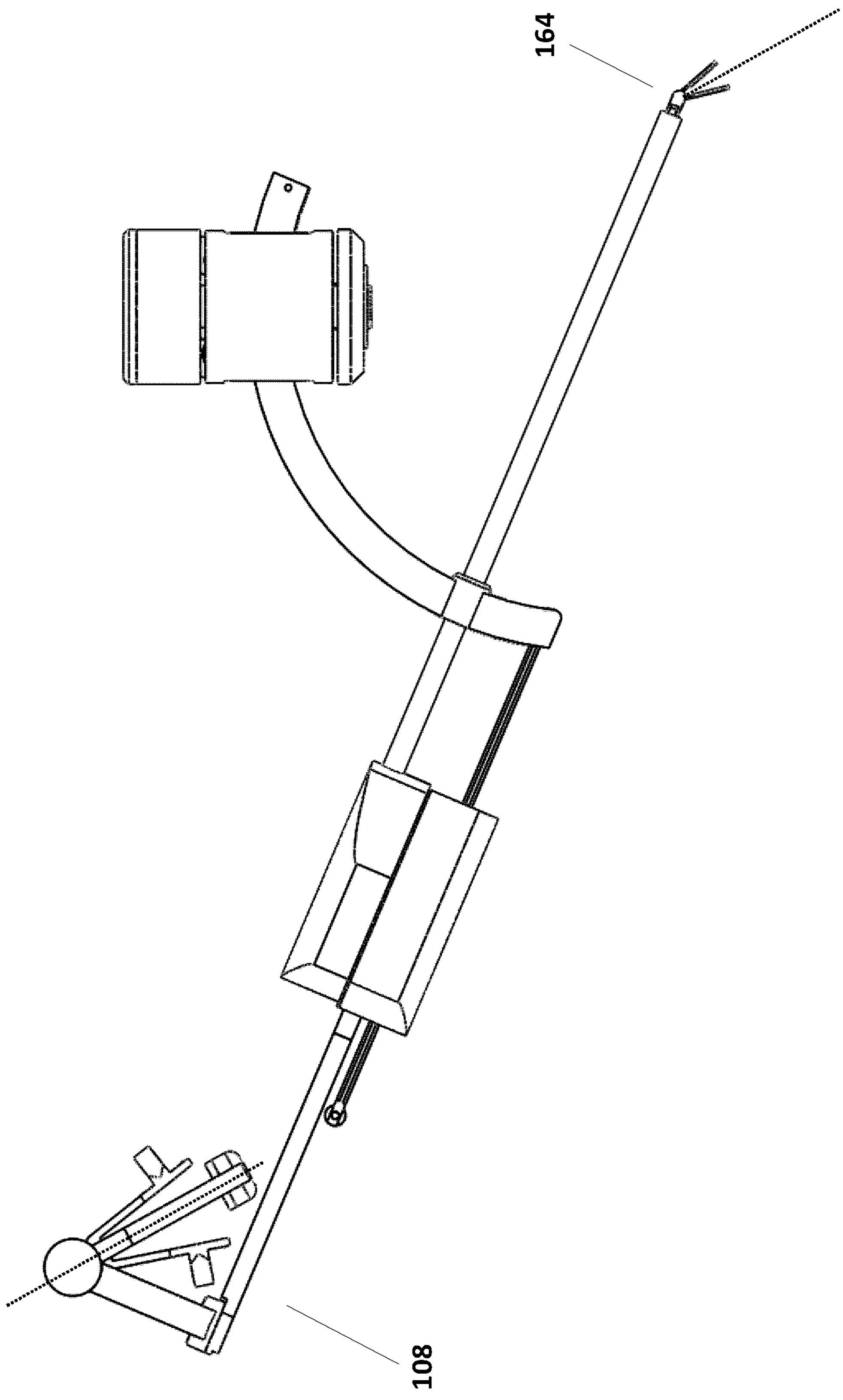
FIG. 18*a* is a side view of another example of the surgical system
Figure 18B:
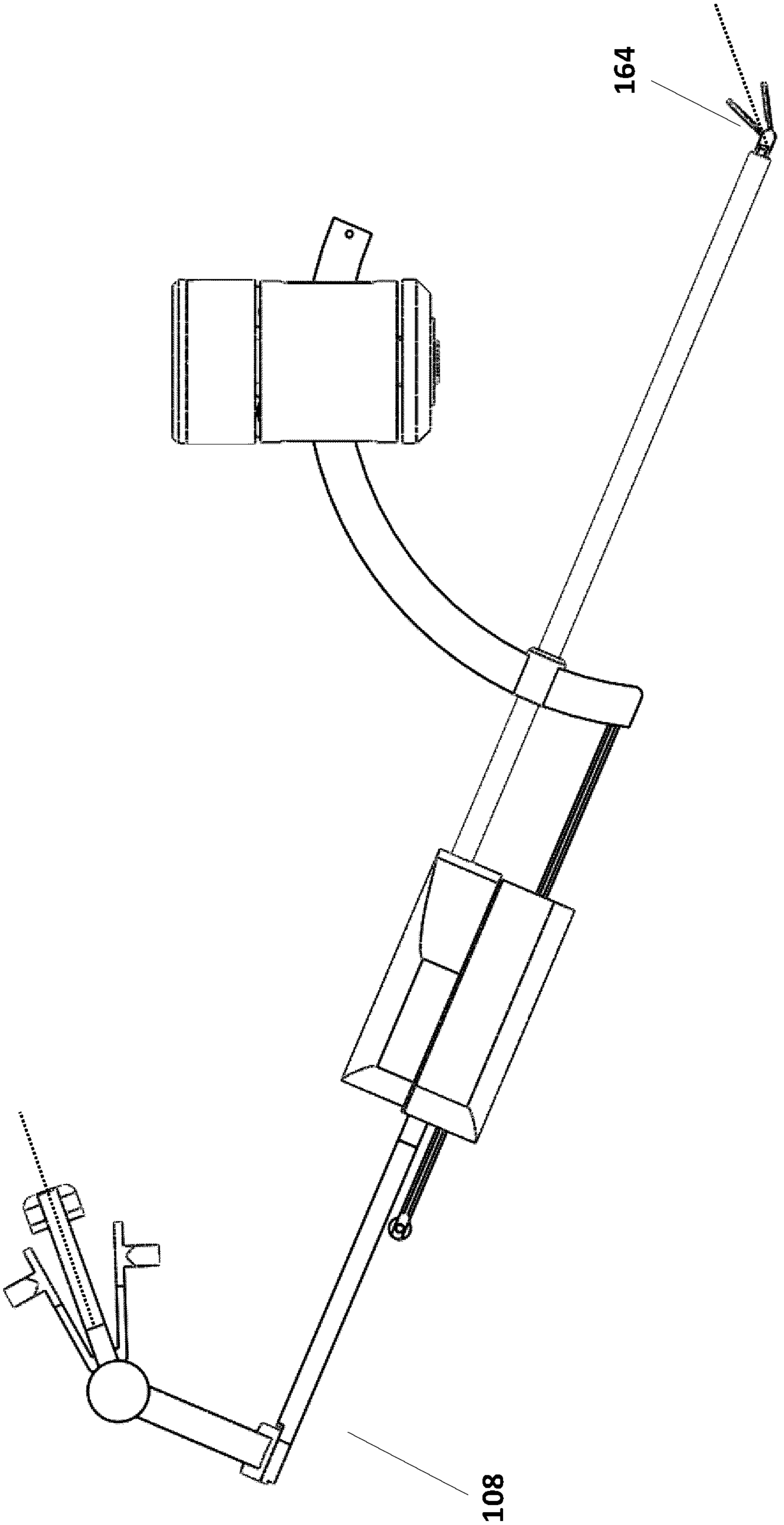
FIG. 18*b* is another side view of the surgical system of FIG. 18*a;*
Figure 18C:
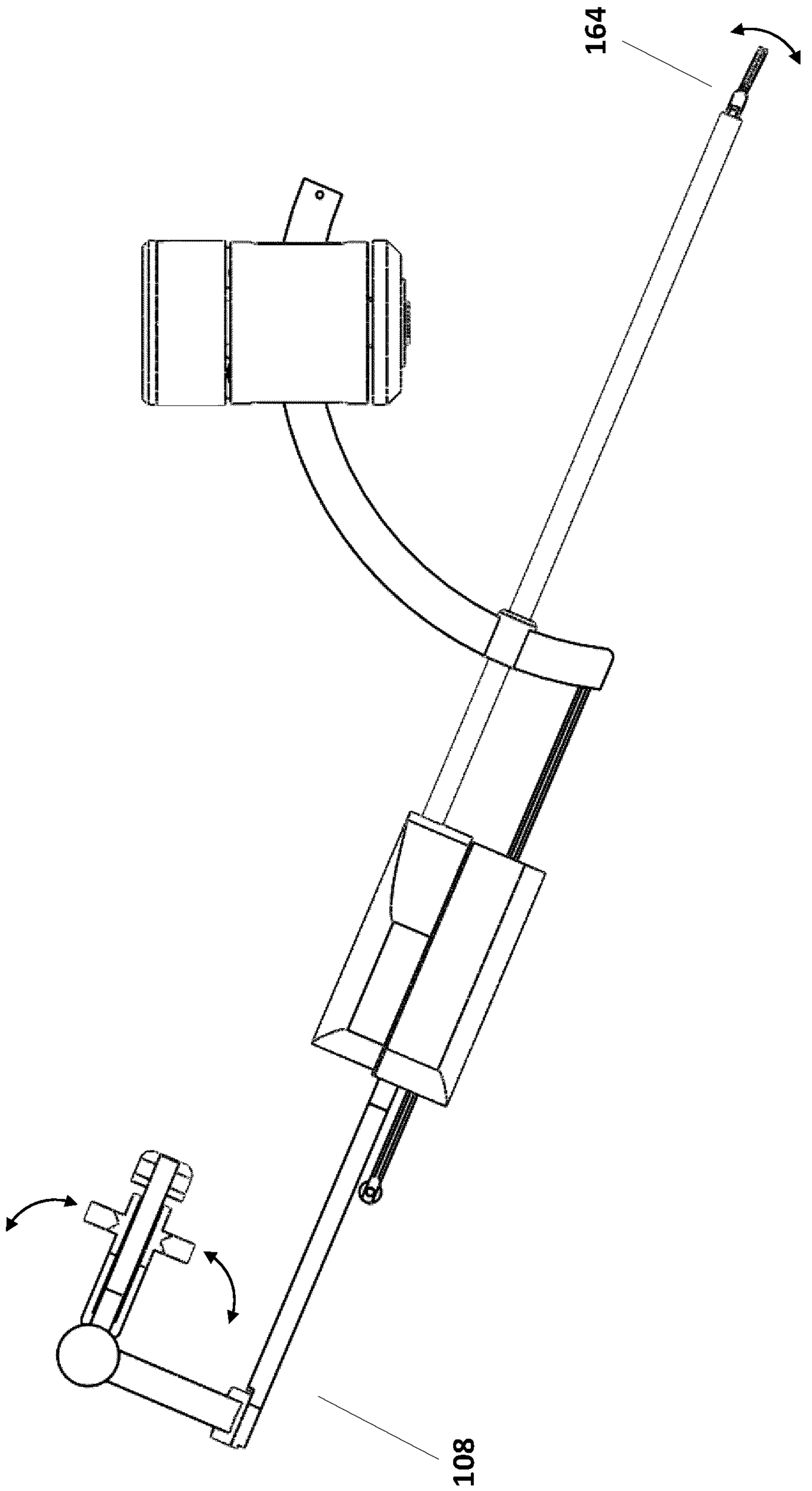
FIG. 18*c* is another side view of the surgical system of FIG. 18*a;*

FIG. 17 is schematic representation of one example of a robotic assist system that can be used with the stabilizing apparatus, as the robotic assist system can be operable to provide robotic-assistance by replicating or translating, through a mathematical transform, the surgeon's hand movements to the wristed end-effector of the surgical instrument, which is referred to herein as local teleoperation. In accordance with this example, the robotic assist system can include handle sensors 410, such as potentiometers or encoders, record the handle orientation of the handle (e.g. handle 108) and information from these sensors are continuously fed into a suitable controller, such as a microcontroller unit 412 in the form of suitable sensor signals. The microcontroller unit 412 can then calculate the desired end-effector wrist orientation based on the orientation of the surgeon handle and generates corresponding controller output signals and can then send the commands/signals to the motor controller 414, which in turns can provide suitable commands and signals to motors 454. The motors 454 preferably each have a motor encoder 418, signals from which can optionally be fed back to the microcontroller 412 via the motor controller 414 in a closed-loop system. The motors 454 can actuate the surgical instrument's end-effector 420 to create the desired end effector orientation based on the outputs of the handle sensors 410. This localized teleoperation can be referred to as a 'human-in-the-loop' system in which the surgeon closes the control loop. For example FIGS. 18*a*, 18*b*, and 18*c* show an example of the localized teleoperation method implemented on the preferred embodiment of the stabilizing apparatus wherein the orientation of the surgeon handle 108 is replicated by the surgical instrument's end effector 164. The example illustrates the synchronization in a single degree-of-freedom and movement in the other degrees of freedom of the handle 108 may be implemented in the end effector 164 in an analogous manner.

Figure 19:
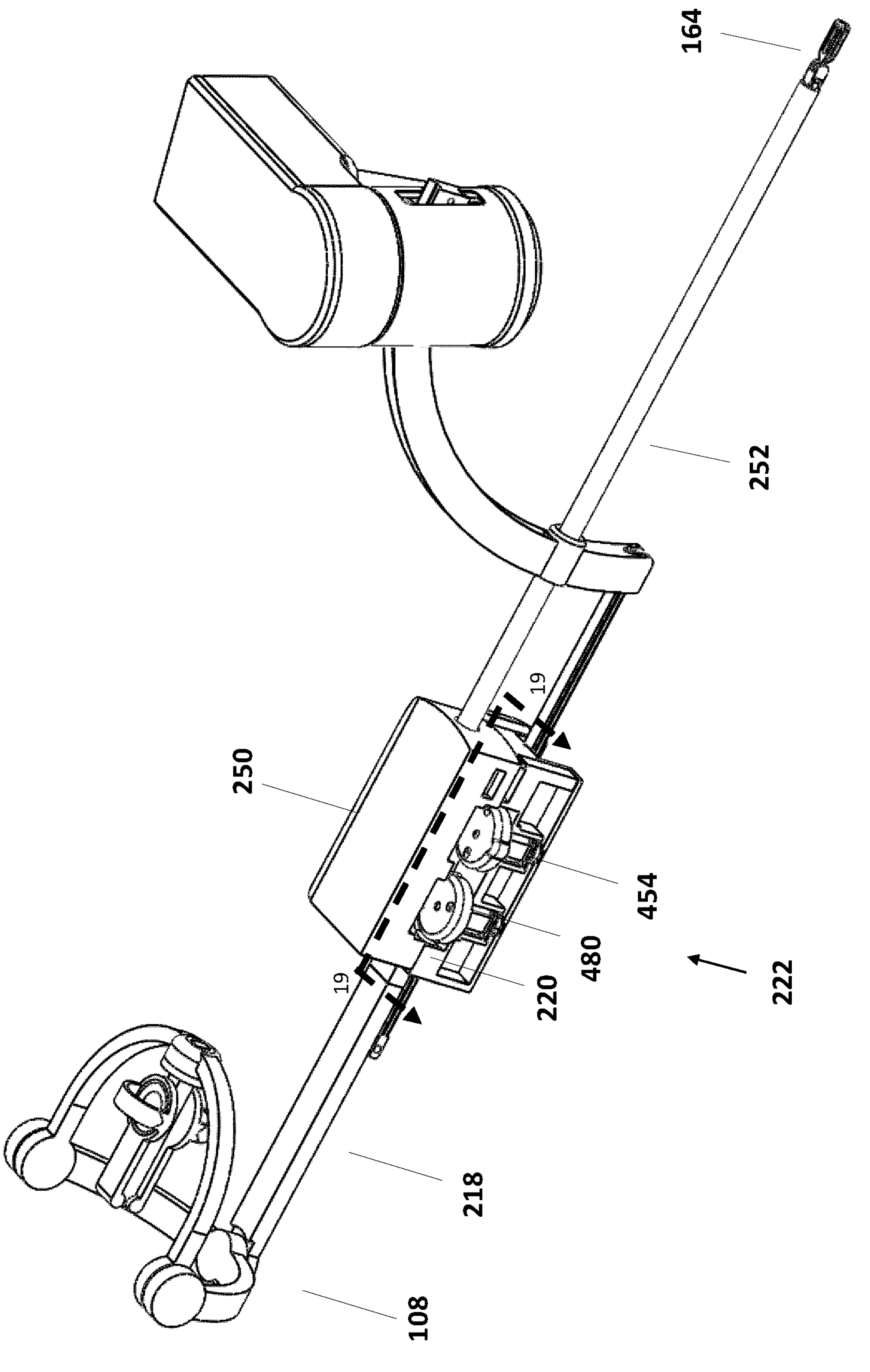
FIG. 19 is a section view of the surgical system of FIG. 18*a;*

Referring also to FIG. 19, in this example the surgeon handle 108 is located at the proximal end of the surgical system and is controlled by the surgeon's hand. The surgeon handle 108 has at least 3 degrees-of-freedom; in the preferred embodiment, this is a yaw-pitch-roll configuration. The angle of each joint in the surgeon handle is tracked via a sensor 410, such as a potentiometer or encoder. The surgeon handle 108 is rigidly connected to the actuation unit 222 via the handle connector 218. The handle connector 218 can have any suitable configuration, and in this example it includes a hollow interior passage that can contain the wires originating from the sensors 410 located in the surgeon handle 108. These wires are connected to a microcontroller 412, which is either housed on the actuation unit 222 or offboard. The microcontroller 412 reads the outputs from the sensors 410 located in the surgeon handle 108 and translates these to motor commands, which are communicated to the motor controller(s) 414, which may also be located on the actuation unit 222 or offboard. The motor controller(s) 414 instruct multiple motors 454 (at least four in the preferred embodiment), which are housed in the actuation unit 222. Rotary motion from the motors 454 is transmitted to the surgical instrument 112 via the attachment interface 220 and carried down the shaft of the instrument 252 via cables, push-rods, or the like, to the wristed end-effector 164.

A power cable running to the actuation unit 222 can provide power to some or all of the electronics and motors and/or some aspects of the control system may run on a battery or batteries or other suitable power supply. The components in the control system may be communicably linked to each other, and optionally to other external equipment using any suitable means of connection, including wires. In an alternative embodiment, the commands from the handle sensors located in the handle may be communicated to the microcontroller unit through a wireless communication method, such as Bluetooth™. In an alternative embodiment, the control electronics (microcontroller and/or motor controllers) may be contained on the base 234 of the system including the support arm 102 to help reduce the mass on the prismatic joint, with either electrical cables connecting the electronics in the base to the actuation unit's motors, or communication performed via Bluetooth™ or another wireless communication protocol.

The device attachment unit, and its sub-components, may be configured to work with one or more different types of surgical devices and instruments by having suitable attachment/connection mechanisms as well as, optionally, having complimentary drive mechanisms that can engage and drive components on the surgical devices. Referring to FIG. 19, the instrument interface 220 and actuation unit 222 are shown with a cross-section view. In this example, attachment interface 220 is provided on the front face of the actuation unit 222 and includes of four identical actuation disks 480, which are powered by the motors 454. These actuation disks 480 interface with corresponding disks on the surgical instrument and provide rotational motion, which is then translated into motion of the end effector. The attachment interface 220 may contain an engagement member in the form of a guide that can mechanically hold the surgical instrument in a friction-fit and ensures that the actuation disks 480 are registered with the corresponding disks on the surgical instrument. Optionally, the actuation disks may be spring loaded to engage with and disengage from the surgical instrument or coupled to the surgical instrument disks via magnetic coupling, gear coupling, friction coupling, or the like.

Figure 20:
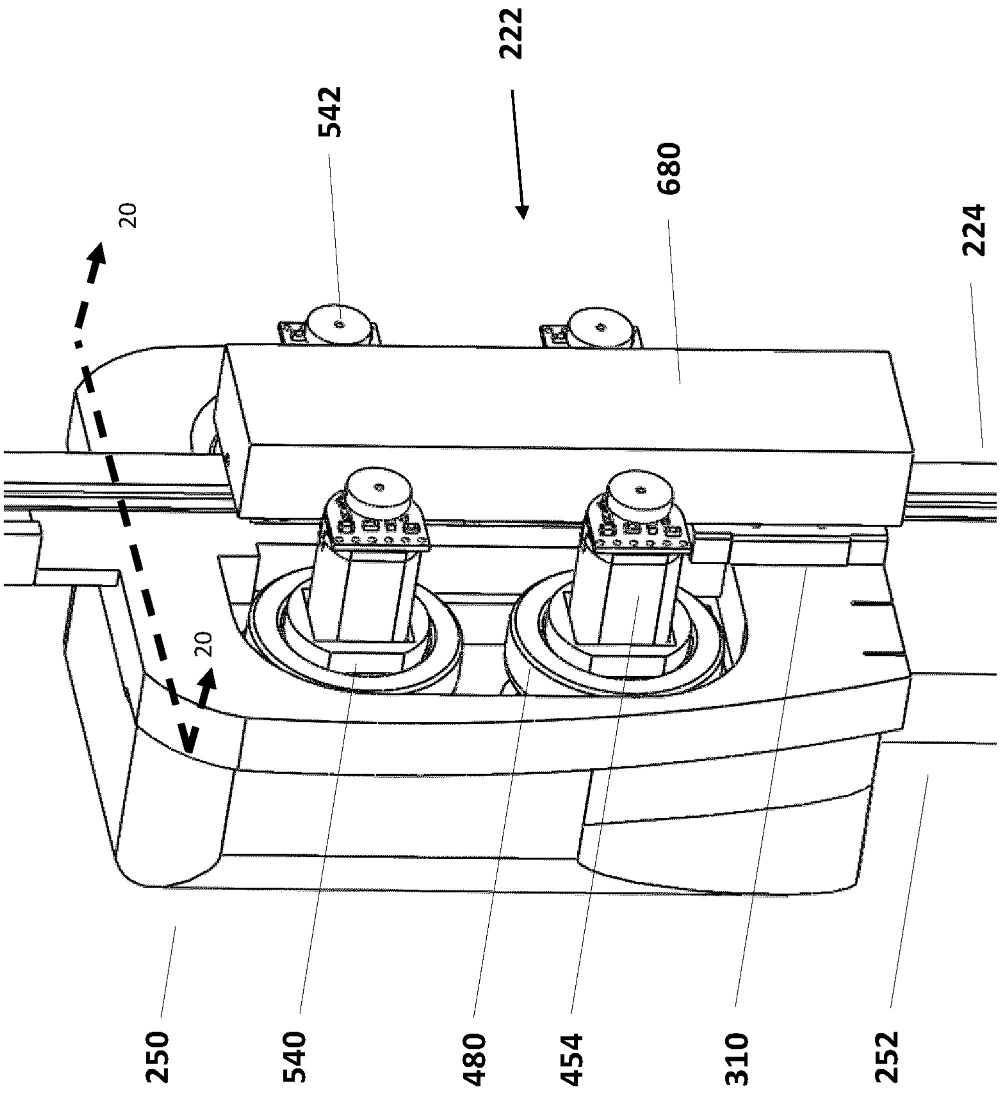
FIG. 20 is a partial cut-away view of one example of a powered actuation unit; taken along line 20-20.

Referring also to FIG. 20, in this example the actuation disks 480 are connected to the motors 454 and the motors 454 are connected to the actuation unit 222 via motor mounts 540, which, in this example, include through holes for connecting two screws to the face plate of the motor. The motors 454 are preferably rigidly fixed to the motor mount 540 and motor encoders 542 can then be attached to the motor 454. The motors 454 have a D-profile shaft, with a corresponding D-profile hole provided on the actuation disk 480. The actuation disk 480 preferably loosely fits on the motor shaft 544 to allow it to slide prismatically. The loose fit may help the actuation disk 480 slide and engage with the corresponding instrument disk. A spring or other suitable biasing member can be located between the back face of the actuation disk 480 and the motor face, thereby providing a force to push the actuation disk 480 into engagement with the corresponding instrument disk. The actuation disk 480 may optionally be retracted to disengage from the instrument disk via the retractor plate. The retractor plate can preferably simultaneously disengages all four disks 480 from the attached instrument when pulled. When the retractor plate is released, the disks 480 maybe urged back into their engagement positions by the biasing member.

Referring also to FIG. 20, the device attachment unit, and actuation unit 222 included therein, can be movably mounted to the track 224 using any suitable mechanism, including a suitable carriage, shuttle, sliders, rollers or the like. The linear actuation mechanism may be preferred in some embodiments as they may help resist thrust loading, thereby keeping the actuation unit 222 firmly secured to the prismatic track 224 even during surgical tasks that may exert relatively high lateral forces on the medical device and/or device attachment unit.

Figure 21:
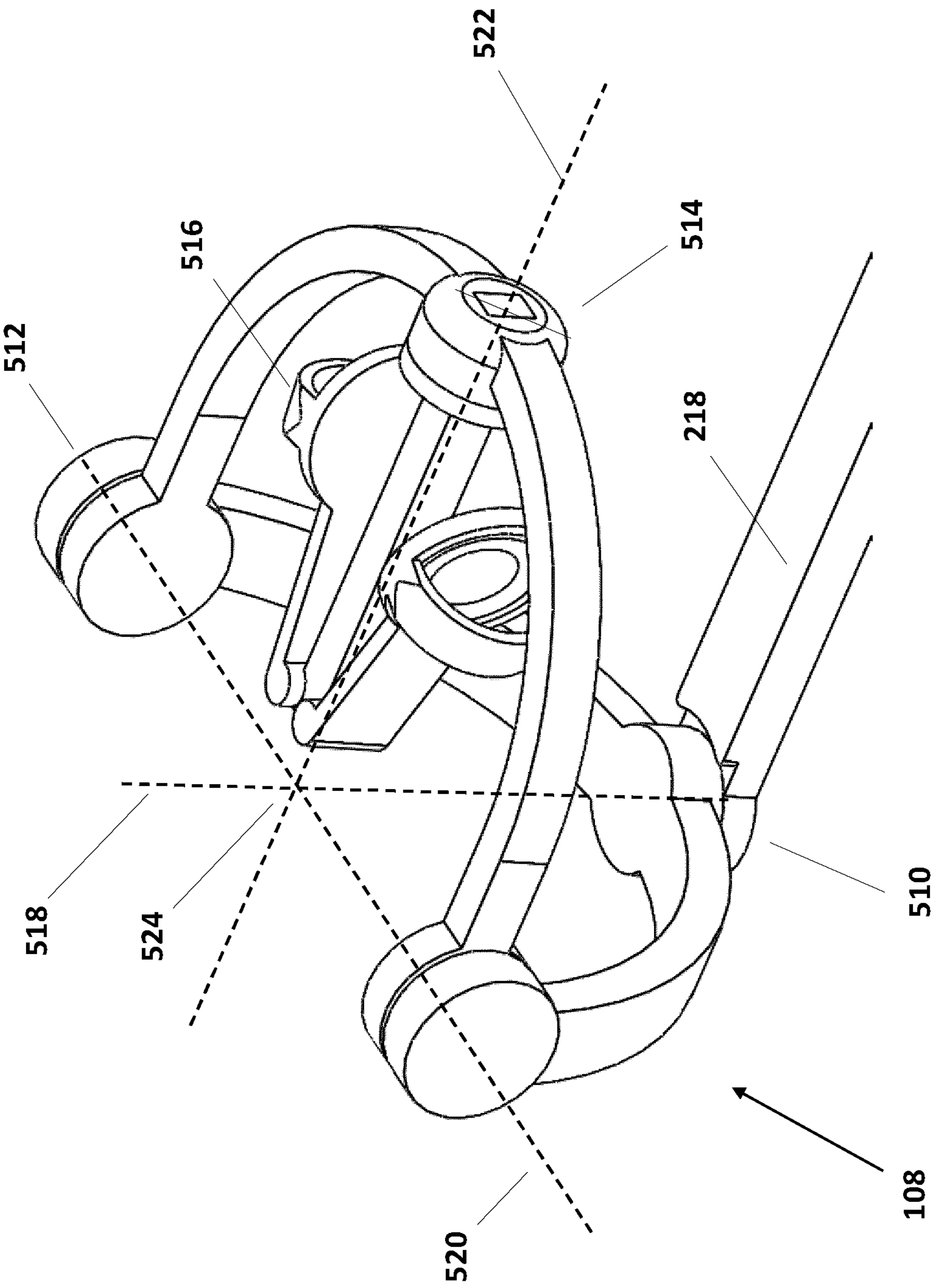
FIG. 21 is an enlarged view of the surgeon handle.

The handle on the stabilizing apparatus is preferably configured so as to be easy to grasp by a user and optionally to resemble some aspects of the design of handles on conventional, hand-held instruments so that it may feel familiar to surgeons with experience using hand-held instruments. Referring to FIG. 21, one example of a surgeon handle 108 is provided in a yaw-pitch-roll configuration. The first yaw joint 510 with axis 518 connects to the pitch joint 512 with axis 520, followed by a roll joint 514 with axis 522. All axes intersect at a remote point 524 to form a spherical wrist configuration. The surgeon grips the handle by finger loops located on the grippers 516. The grippers 516 allow for an additional degree of freedom for actuating/activating instrument functions, depending on the attached surgical instrument. For example, the grippers 516 can be used to control the open and closing grasping motion of the end-effector of the attached surgical instrument. The grippers may contain additional buttons to activate additional instrument functions, such as cautery on energy instruments. Each joint contains a sensor, such as a potentiometer or encoder, with hollow links to route the electrical wires through the handle to avoid interfering with the surgeon's hand. The electrical wires are then routed through the handle connecter 218, which is also hollow, to the actuation unit 222. The handle shown in the preferred embodiment is a 'gimbal' style.'

Figure 22:
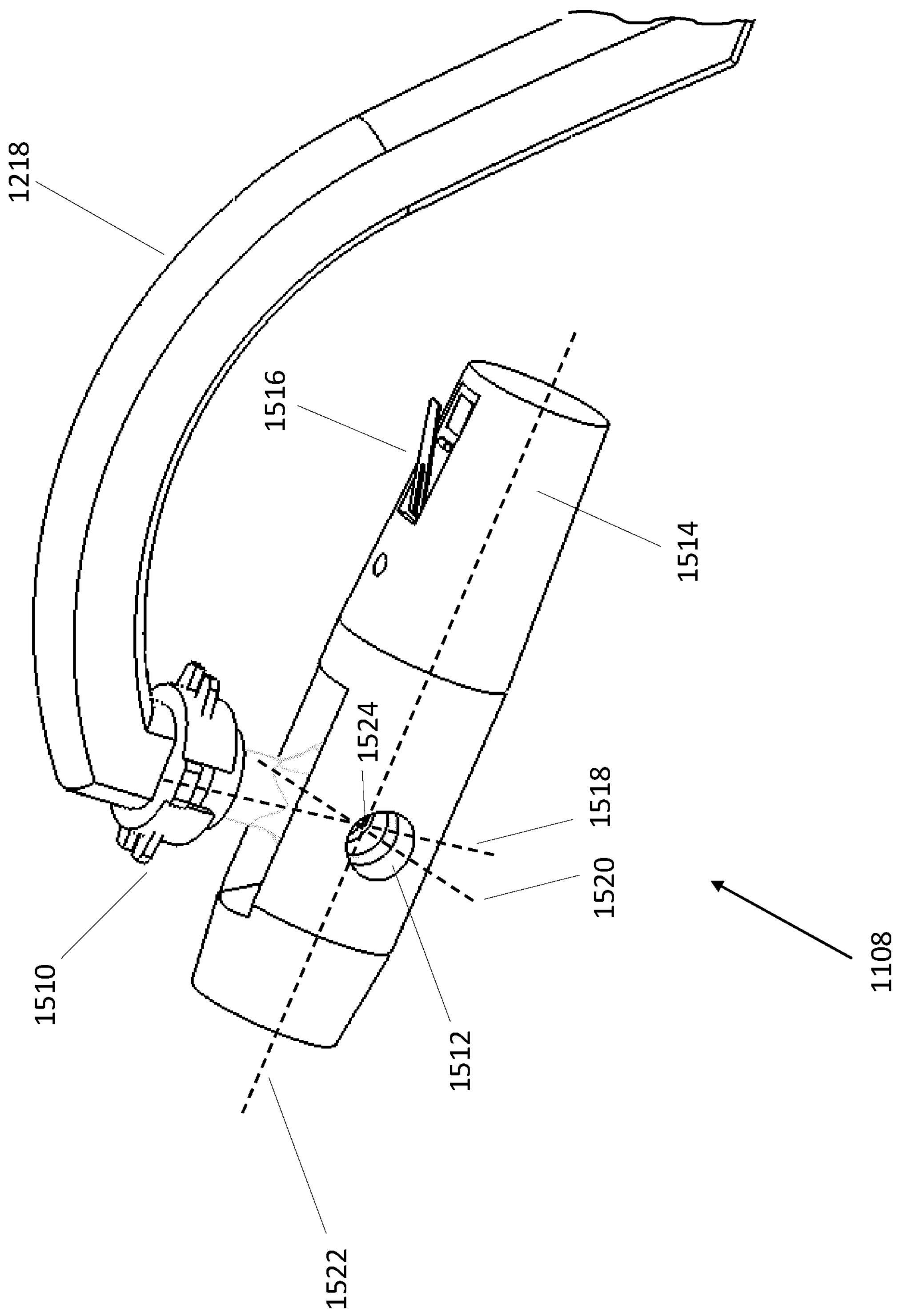
FIG. 22 is an enlarged view of an alternative surgeon handle.

Referring to FIG. 22 is another example of a handle 1108. That is, in this example the handle 108 has a yaw joint 1510, rotatable about yaw axis 1518, that connects to the pitch joint 1512 that is movable about pitch axis 1520, and a roll joint 1514 that is movable about the roll axis 1522. The handle 1108 is generally similar to handle 108 and like features are identified using like reference characters indexed by 1000. In this example, the handle axes 1518, 1520 and 1522 are configured to intersect at a common point 1524 which can help provide a spherical wrist configuration for the handle 1108. Embedded in the last roll link in this example is a button 1516 for an additional degree of freedom or for actuating/activating additional instrument functions, depending on the attached surgical instrument. For example, the button 1516 can be used to control the open and closing grasping motion of the end-effector of the attached surgical instrument, or for activating the delivery of bipolar cautery. The button 1516 may be a mechanical switch, a capacitive element, or the like. Each joint may optionally include a sensor, such as a potentiometer or encoder, and preferably can be configured with hollow links to route the electrical wires through the handle 1108 to avoid interfering with the surgeon's hand. The electrical wires are then routed through the handle connecter 218, which is also preferably hollow, to the actuation unit 222.

The handle 1108 is a 'pen-style' grip in which the grip of the surgeon's hand mimics how a pen is held. There are several alternative embodiments of the surgeon handle not limited to the 'pen-style.' Other alternatives may include a pistol-grip style handle with a 3-degree-of-freedom joint located either distal or proximal to the handle and/or a handle with a virtual pivot point at the same location as the centroid of the user's wrist. Optionally, the handle may have more than three degrees of freedom for controlling higher degree of freedom instruments. In yet another embodiment, the handle may contain additional sensors for advanced functionality, such as locking joints on the RCM mechanism or adjusting electronically controlled dampening of the RCM mechanism. In another embodiment, the handle may have a 'dead-man switch' style sensors, such as a trigger or capacitive touch sensor, which would serve to lock the RCM mechanism unless the surgeon was holding the handle, to prevent the surgical instrument's end-effector from moving unintentionally. In another embodiment, the handle, as it is understood to be in the context of this invention, may be a glove that at least partially fits over the hand of the user.

The handle connector 1218 may also have a number of alternative embodiments, such as the ability to be made reconfigurable and adjustable, for example the ability to add a lateral offset between the surgeon handle 108 and the actuation unit 222. Since the control method is completely fly-by-wire, and no mechanical actuation occurs through the handle connector (e.g. cables) there are fewer limitations on the design of the handle 108 and 1108. A reconfigurable or adjustable handle may be beneficial in certain operations where the surgeon typically must operate the instruments from an awkward and fatiguing position, such as during a prostatectomy.

Figure 23:
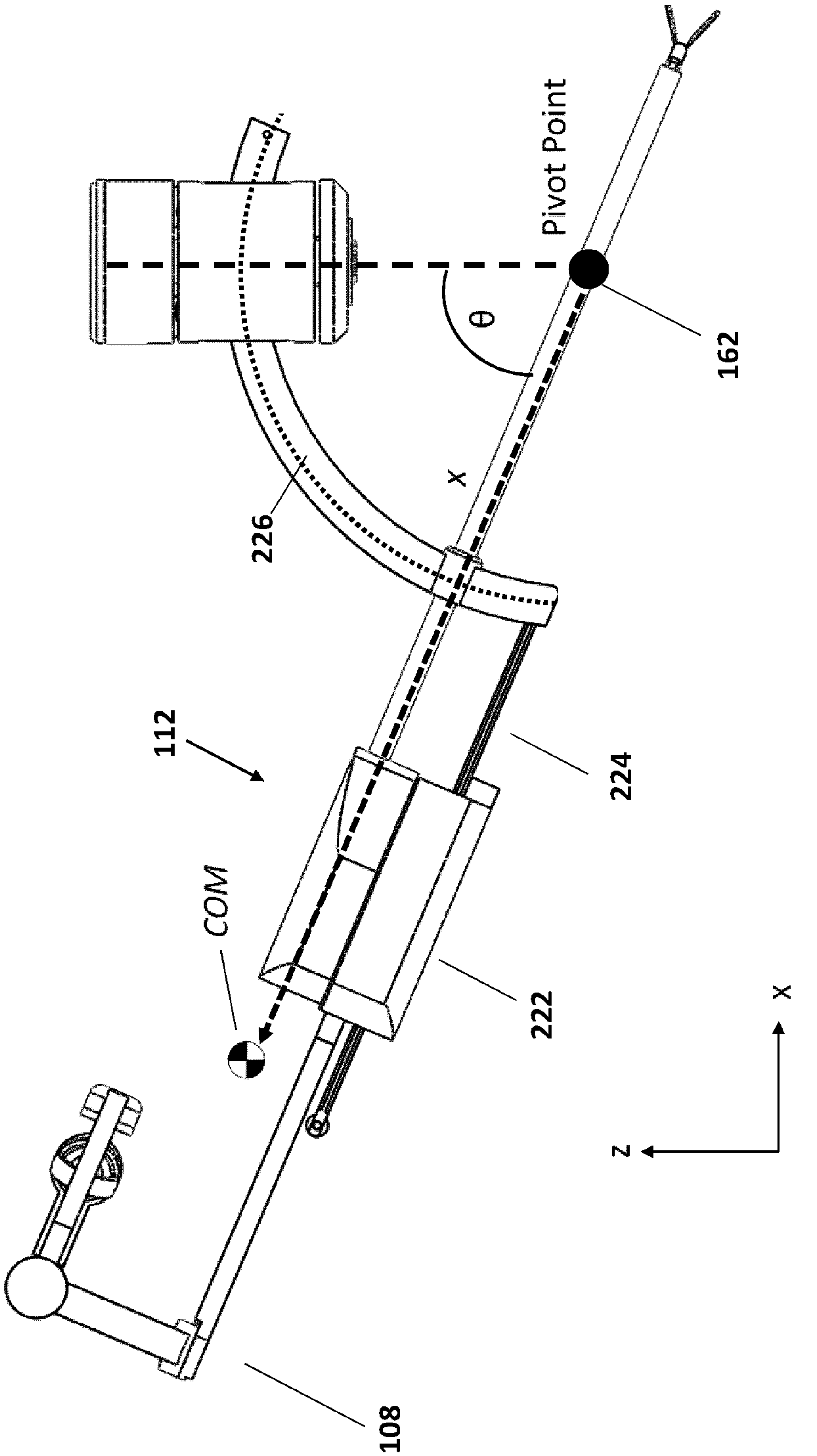
FIG. 23 is a side view of the surgical system where the center of mass of the moving components is highlighted.

Optionally, as described herein, one or more of the degrees of freedom and/or joints in the stabilizing apparatus can be counterbalanced using a suitable counterbalancing apparatus. The counterbalancing apparatus is preferably passive, i.e. non-motorized, so that it can be freely moved in response to a manual input from a user (e.g. pushing or pulling on the handle 108) without needing to engage a motor or other drive mechanism. This type of counterbalancing may be desirable in some embodiments of the surgical system as the robotic/assistive components, such as the motors, electronics, and sensors, can add significant weight to the surgical system and so counterbalancing system(s) are implemented in the preferred embodiment. Counterbalancing may help reduce and possibly eliminates or minimizes any input force required from the surgeon to hold the surgical instrument in a steady position. The force required to counterbalance the system is a function of the mass and the position of the surgical instrument. More specifically, the mass includes any components that are able to move in the X-Z plane, as shown in FIG. 23, including but not limited to the surgeon handle 108, prismatic track 224, arcuate track 226, actuation unit 222, and attached surgical instrument 112. Preferably, as shown in this example, the stabilizing apparatus is set up such that the rotation axis 284 of the revolute joint 228 is substantially vertical (i.e. parallel with the gravity vector) when the system is in use. In this arrangement the stabilizing apparatus does not require any material counterbalancing about the revolute joint 228, and that only the gravity forces created by the arcuate track 226 and prismatic track 224 require counterbalancing. The term center-of-mass (COM) herein refers to the center of mass of all components that require counterbalancing due to their movement along either the arc or prismatic joints. The COM is illustrated schematically as being located between the base of the surgical instrument and the surgeon handle for simplicity, as depicted in FIG. 23, but may be in a different position in different examples of the surgical system.

Figure 24B:
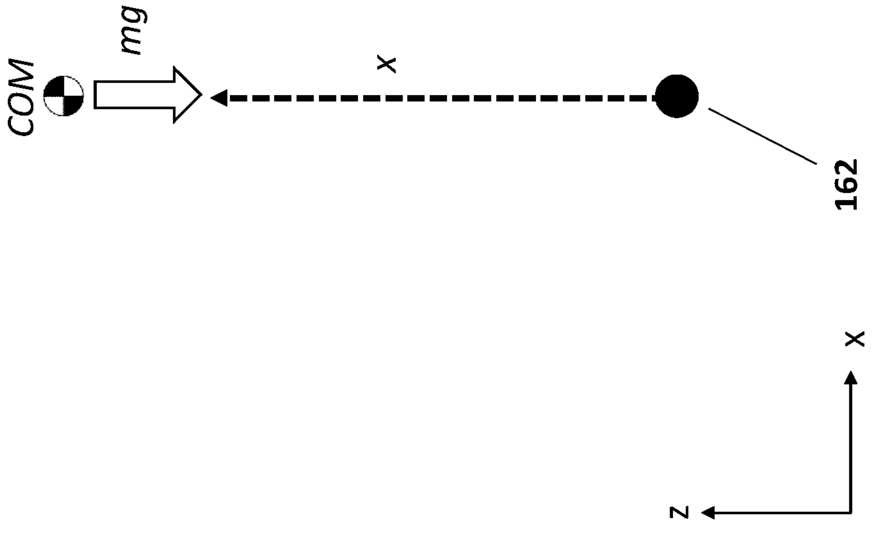
FIGS. 24*a*-24*b* are schematic illustrations showing an overview of torques that may be generated in the surgical system.
Figure 24A:
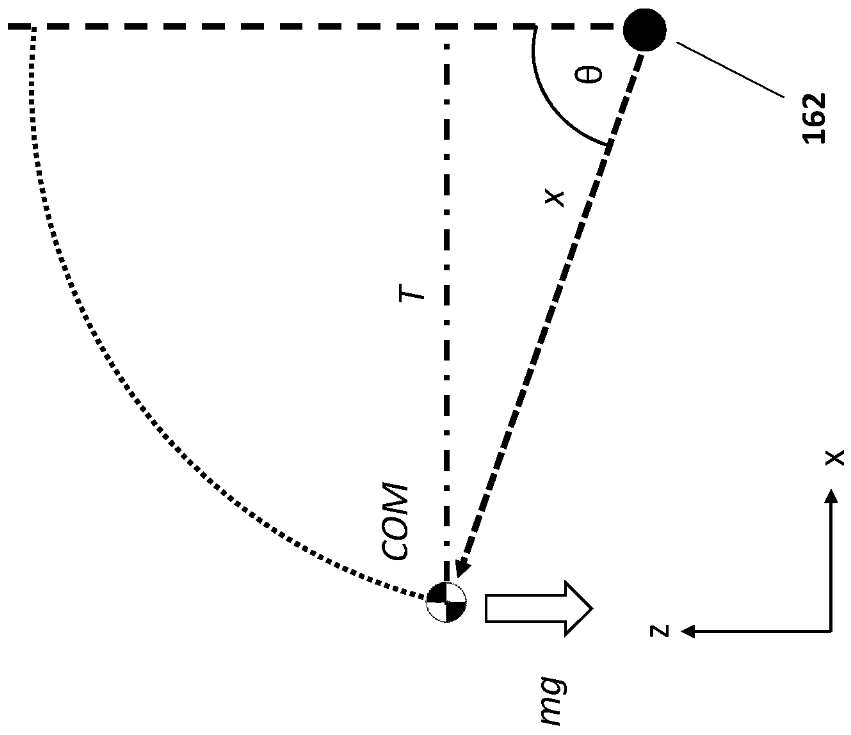

In this arrangement, the COM creates a torque about the remote-center-of-motion 162 and this torque changes as the surgical instrument and associated components are moved along either the prismatic track 224 or the arcuate track 226. As shown in FIG. 23, the angle of the COM along the arcuate track 226 is labeled θ, and the position of the COM along the prismatic track 224 measured from the remote-center-of-motion 162 is labeled x. As shown in FIG. 24*a* which shows a simplified system representation, the torque generated depends on the lateral distance (“T”) from the COM to the vertical axis of the remote-center-of-motion 162 and the force (“mg”) which depends on the mass of the relevant components. The torque is the product of T and mg. As either x or θ increases, so does the length of T, increasing the torque about the remote-center-of-motion 162. The torque reaches a maximum as θ approaches 90 degrees, when the surgical system is in a completely lateral position, and when x is maximized. FIG. 24*b* illustrates as special case with θ set at 0-degrees; the COM of the instrument is directly vertical above the remote-center-of-motion 162, reducing T, or the normal distance between the COM and the vertical remote-center-of-motion 30 axis, to zero. In other words, at 0-degrees θ, the joint created by arcuate track 226 does not contribute to the counterbalance requirements. In this arrangement, the torque acting about the remote centre of motion 162 increases as an angular position of a first end of the arcuate track relative to the hub, i.e. θ, changes from about 0 degrees to about 90 degrees. Optionally, as described herein, the counterbalancing system can include a biasing apparatus that is configured so that a magnitude of the biasing force (to help counterbalance the gravity loads) can increases as the angular position of a first end of the arcuate track relative to the hub changes from about 0 degrees to about 90 degrees so that the biasing force remains substantially equal (e.g. within about 10% of each other, between about 10% and 20%, and optionally greater than 20%) to the magnitude of the torque T when the angular position of a first end of the arcuate track relative to the hub is between about 0 degrees to about 90 degrees. Although no torque is generated about the remote-center-of-motion 162, the components which move along the prismatic track 224 are co-linear with the gravity vector and require counterbalancing.

Figure 25:
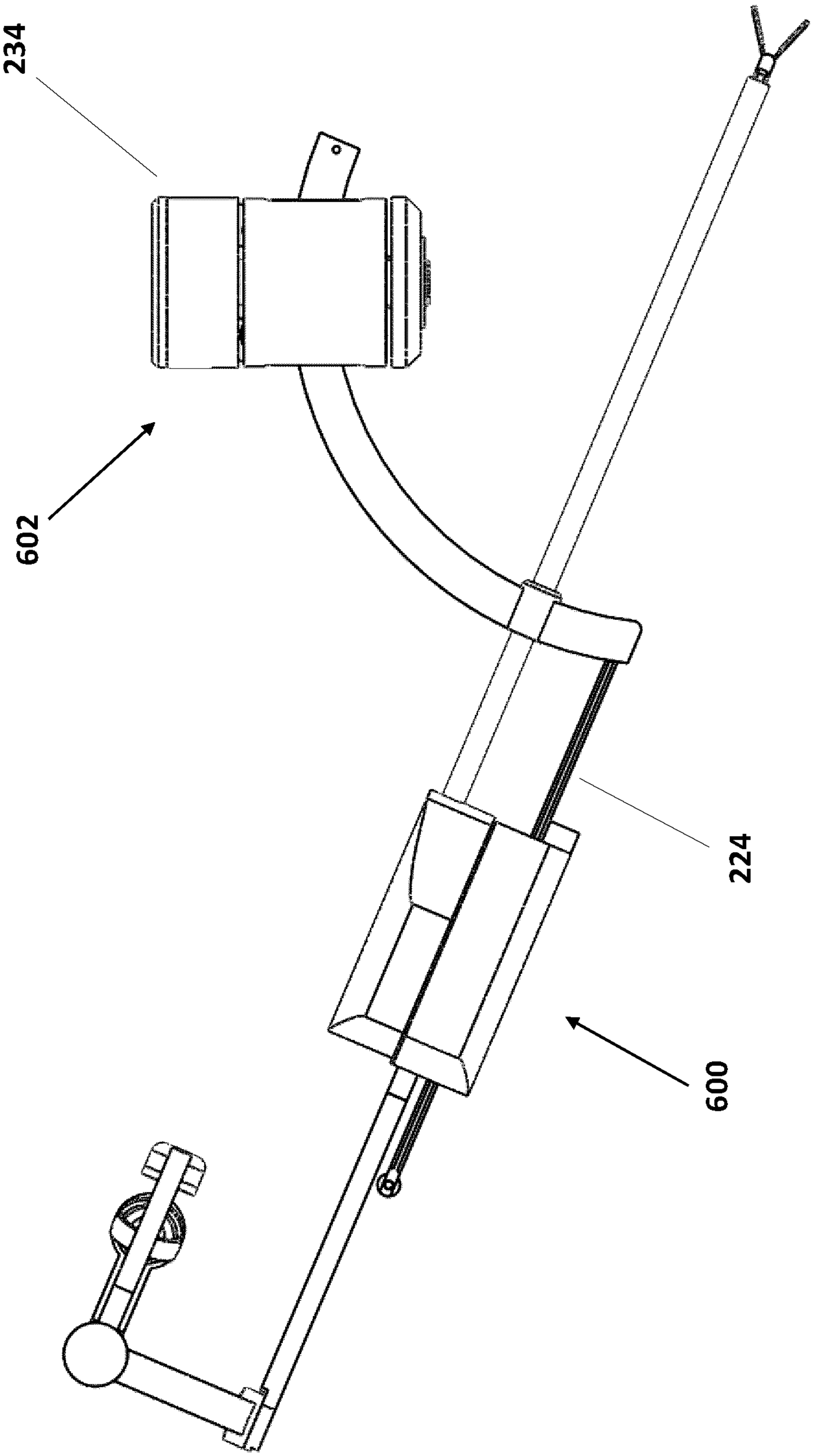
FIG. 25 is a side view showing an overview of the counterbalancing system.

FIG. 25 shows an overview of one example of a suitable counterbalancing system that can be implemented in the surgical system 100. In order to counterbalance the illustrated example of a surgical system, two separated counterbalances are implemented in the preferred embodiment. First, a prismatic pulley-mass counterbalance system 600 is implemented along the prismatic track 224. The mass of the counterbalance weight required for the prismatic counterbalance system 600 is chosen so that it is at least substantially equal to the sum of the masses of all components that are able to move along the prismatic track 224, which includes the actuation unit 222, the surgical instrument 112, and the surgeon handle 108 in this example. The function of the prismatic counterbalance system is preferably two-fold: (1) to help counterbalance the prismatic motion of the attached surgical instrument (i.e. surgical instrument insertion and retraction), and (2) to help maintain a substantially constant center-of-mass of all components that move along the prismatic track, including the attached surgical instrument regardless of their linear position. Using the system 600 to help provide this substantially constant center-of-mass helps facilitate the use of the second counterbalance system 602 acting on the arcuate track. In the illustrated examples the arc counterbalance system 602 is a cable-driven, spring-cam counterbalance system located primarily in the base 234 of the stabilizing apparatus. The second counterbalancing system 602 is design to help neutralizes the torque generated about the remote-center-of-motion 162. This two part counterbalance approach implemented in the preferred embodiment essentially decouples the counterbalancing requirements of the prismatic track 224 and the arcuate track 226, and may simplify the design and operation of each system.

Figure 26B:
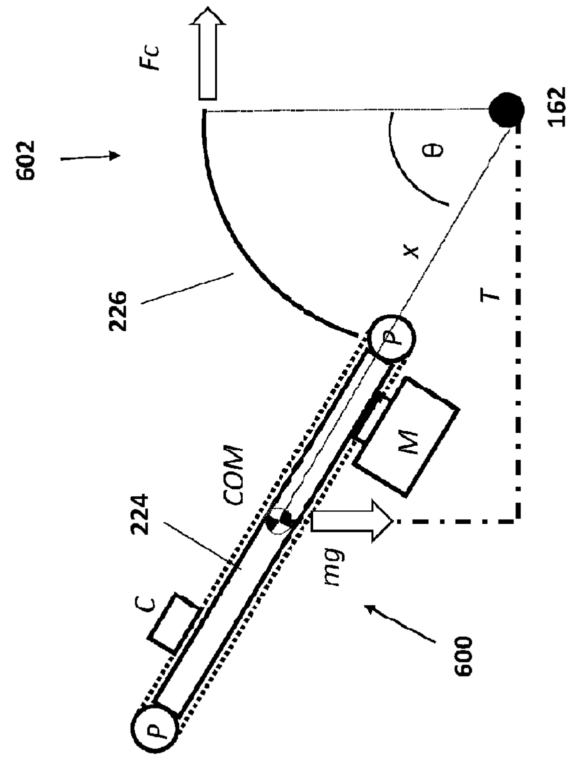
FIGS. 26*a*-26*b* are schematic views illustrating one example of a translation counterbalance for the surgical system.
Figure 26A:
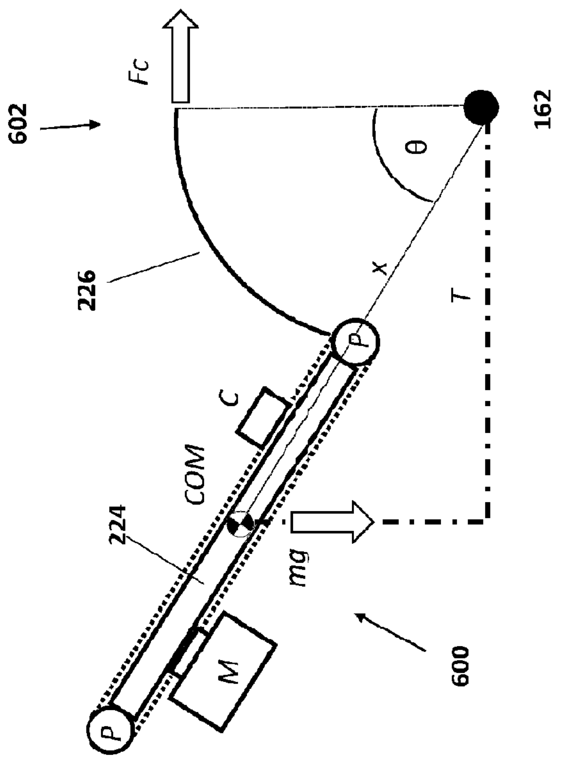

Referring to FIG. 26*a* and FIG. 26*b* show schematic representations of the prismatic, translation counterbalance system 600 and the spring-cam, arc counterbalance system 602. In this illustration the prismatic pulley-mass counterbalance helps provide a relatively constant COM as the prismatic components such as the handle and actuation unit—together represented by unit M in this figure—move along the prismatic track 224. A sufficiently equal counterbalance mass, preferably made of a denser material (therefore requiring a smaller volume) is represented by “C.” The prismatic track 224 contains guide members in the form of pulleys at either end (“P”), and the mass M and mass C are connected via cables. As the mass M travels in either direction along the prismatic track 224, the mass C moves in the opposite direction. Since the masses are practically equal, the spatial location of the COM relative to the prismatic track 224 is maintained substantially constant. This is depicted in FIG. 26*b*, in which the mass M has moved toward the RCM, and the mass C has moved in the opposite direction, in comparison to the positions of the masses in FIG. 26*a* but the COM remains in the same position. As a result of this relatively fixed position of the COM, the torque generated about the RCM by the translating components is maintained at a substantially constant level. This generated torque is then counterbalanced by the spring-cam counterbalance system 602, which can generate a generally constant and equal but opposite torque represented by "Fc" via a cable that runs along the arcuate track 226.

Figure 27:
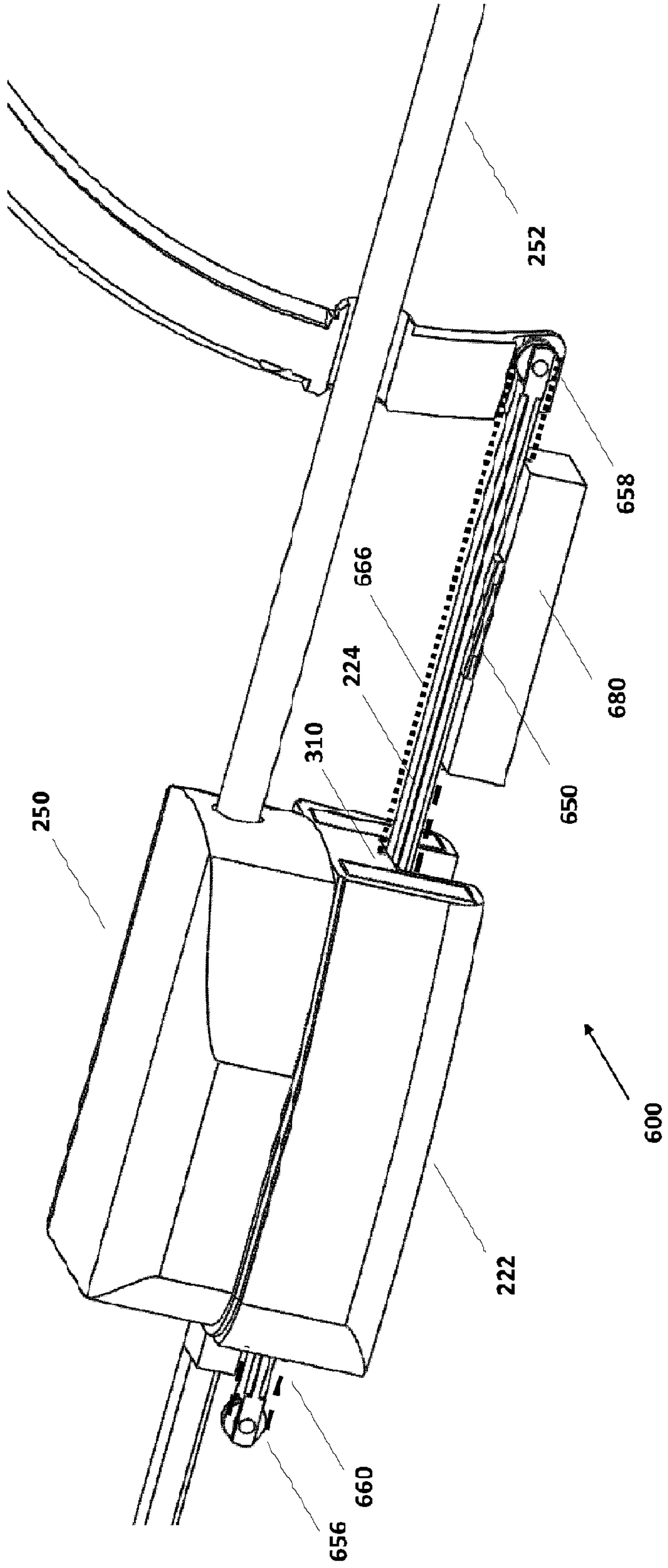
FIG. 27 is a side view of one example of a translation counterbalance for the surgical system.
Figure 28:
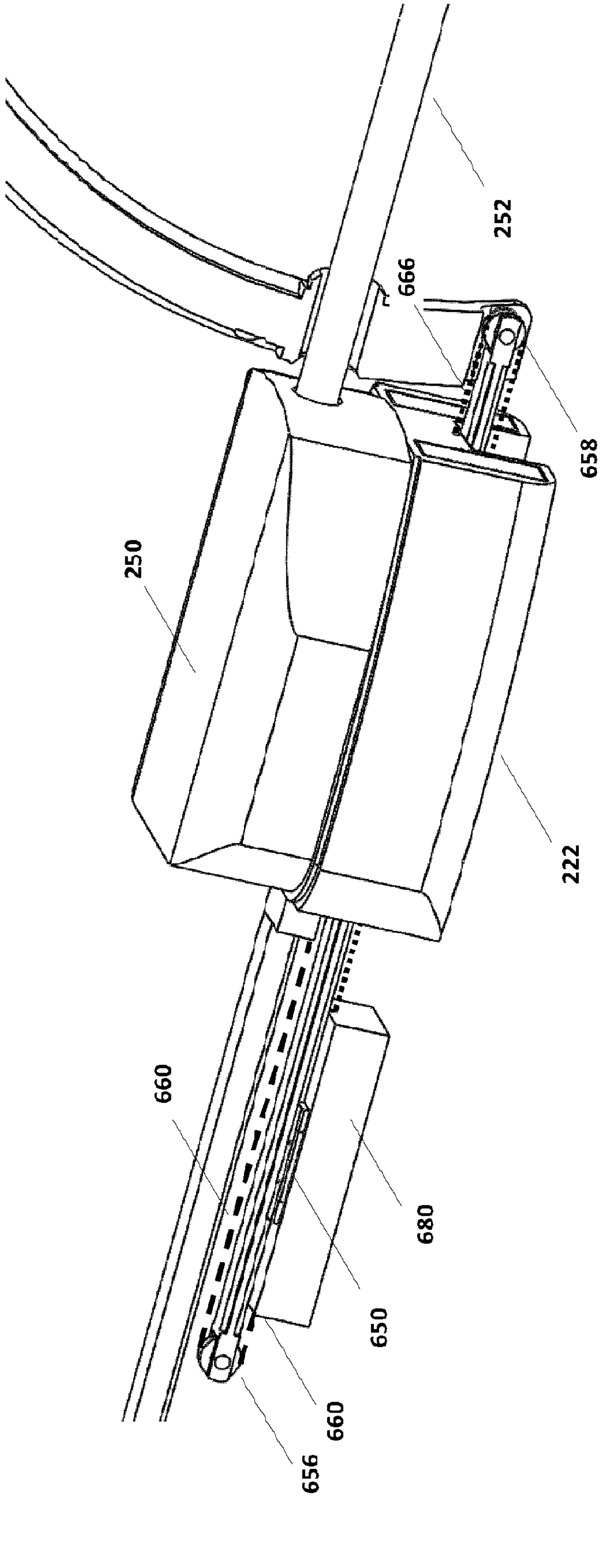
FIG. 28 is a side view of one example of a translation counterbalance for the surgical system of FIG. 27.

FIGS. 27-28 shows a preferred example of the prismatic counterbalance system 600. In this example a carriage 650 runs along a dedicated counterbalance track on the back side of prismatic track 224. The linear carriage 650 holds the counterbalance weight 680, which is sized to equal the weight of all moving components on the prismatic track 224. At either end of the prismatic track 224 are guide member/pulleys 656 and 658. A cable 660 is connected to the carriage 650, wraps around pulley 656, and is terminated on the actuation unit 222. A second cable 666 is connected to the opposite end of carriage 650, wraps around pulley 658, and is terminated on the opposite end on the actuation unit 222. The cable system can be tightened and attached at the connection points on the carriage 650 and actuation unit 222 using a variety of systems, such as a turnbuckle, capstan, or the like, to achieve the proper cable tension.

Figure 29:
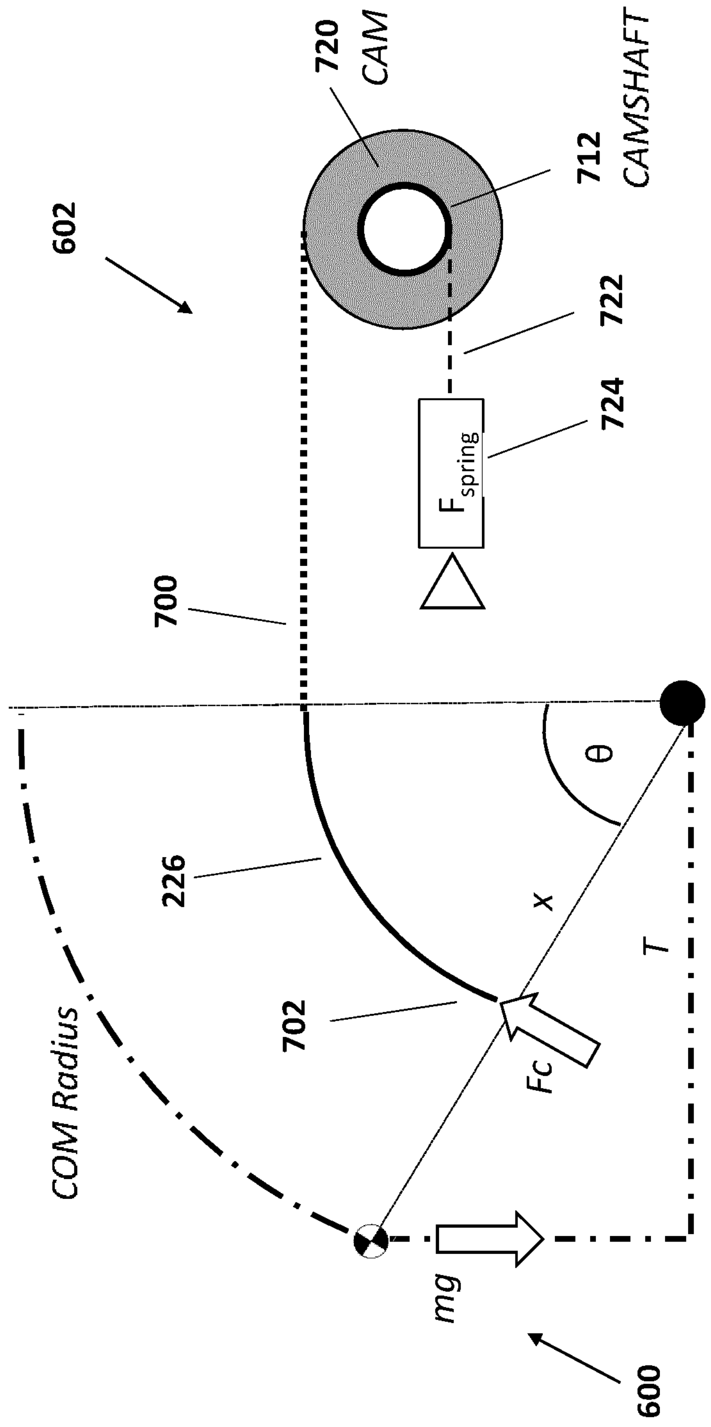
FIG. 29 is a schematic view showing one example of counterbalance system for the surgical system.

Referring also to FIG. 29, it is understood that the COM remains at the same location along the prismatic track 224, and therefore creates a constant COM radius as indicated in FIG. 29. The spring-cam counterbalance system 602 can then preferably be configured/calibrated to substantially neutralize this torque for any angle θ. In the illustrated example, a flexible tension member, such as a wire or cable 700, runs along the arcuate track 226 and is attached to one end of the arcuate track 226 at location 702, that is at the same end of the track as the linear translation apparatus. The opposite end of the cable 700 wraps around and is connected to cam 720. The cam 720 is rigidly attached to a camshaft 712 which is supported by bearings, thus allowing to rotate both cam 720 and camshaft 712 to rotate as a single unit. A second tension member, such as cable 722, wraps around and is connected to camshaft 712 and connected at the other end to a suitable biasing member, such as an extension spring 724, elastic band and the like.

The cable 700 is, in this arrangement, effectively shortened by the same ratio as the ratio between the diameters of cam and camshaft, resulting in a significantly shorter output cable 722. If the original cable length was maintained it may require a spring with a travel length similar to the arc length of arcuate track 226. By effectively reducing the cable length to cable 722, a significantly smaller spring can be implemented. This may help reduce the overall size of the surgical system. In an alternative embodiment, a constant force spring is wrapped around the cam to apply the necessary torque for counterbalancing. In an alternative embodiment, a gearbox system may be used to achieve a reduced cable length.

The spring in this example generates a force ("Fspring") which acts on the cable system and generates a force at the end of the arcuate track 226 in the tangent direction ("Fc"). The cam, camshaft, and spring are designed such that the torque generated by Fc is equal and opposite to the torque generated by mg. If this balance is maintained the system can be considered to be fully counterbalanced.

Figure 30:
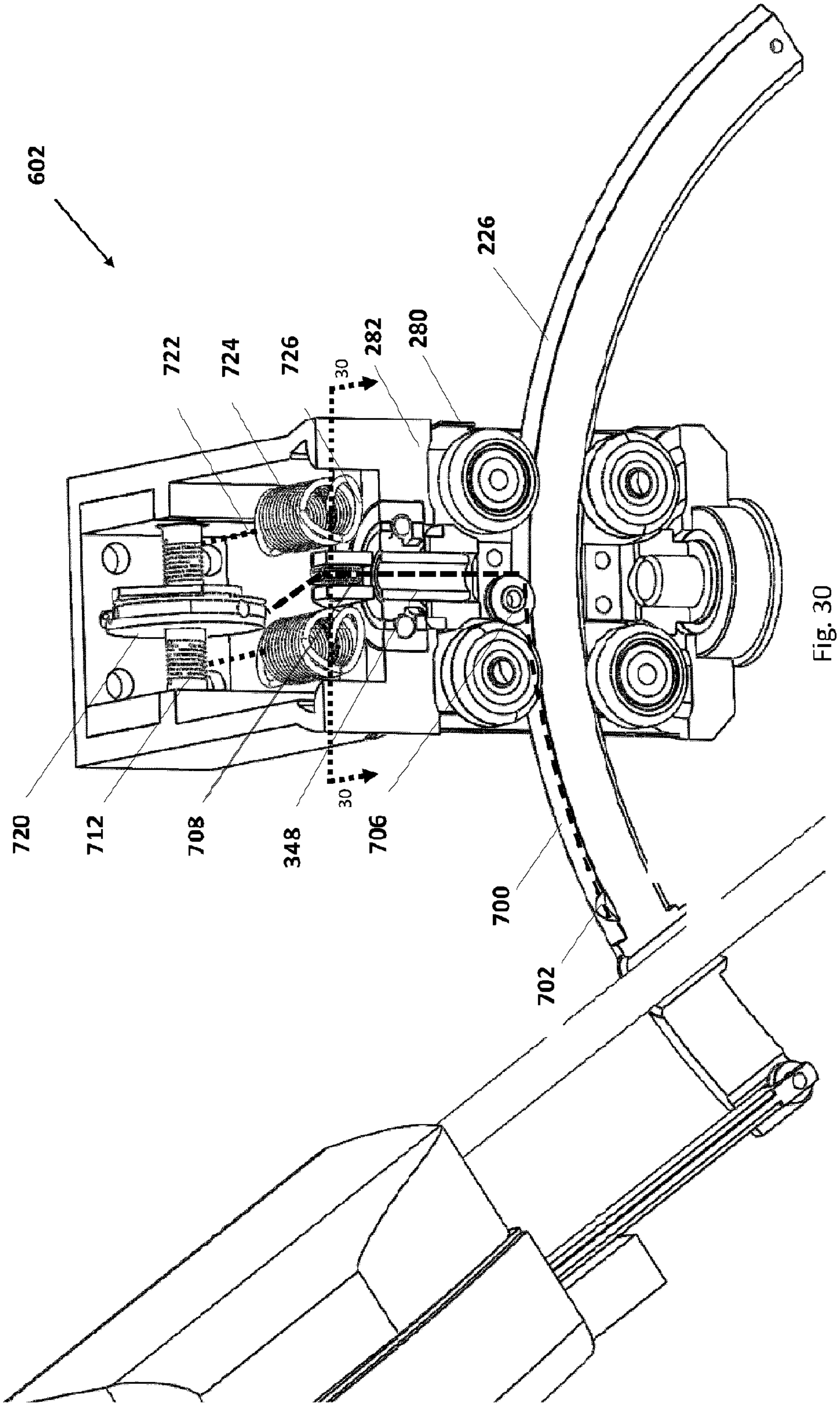
FIGS. 30-31 are section views showing one example of a spring-cam counterbalance system for the surgical system.
Figure 31:
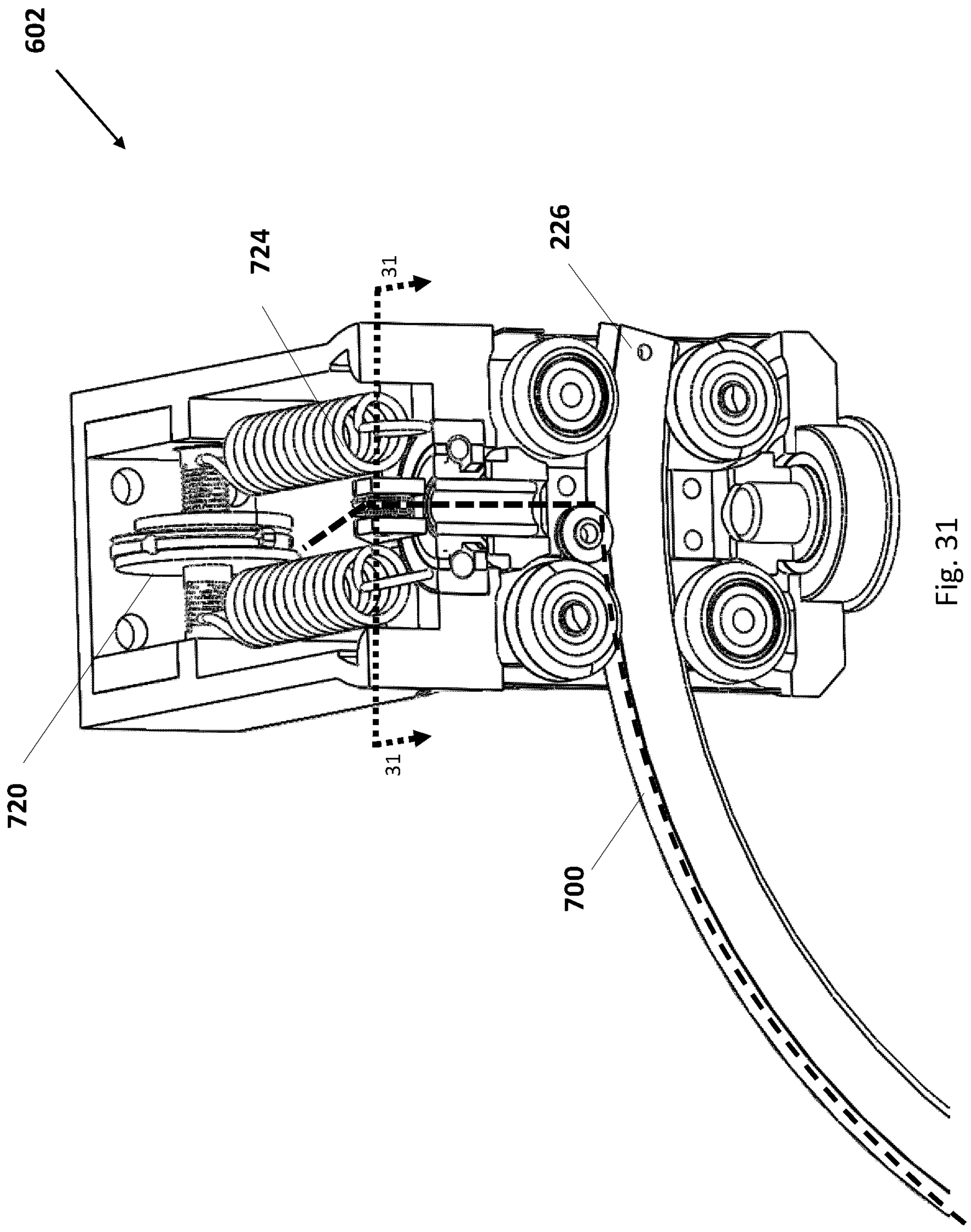

FIGS. 30-31 show a cross section of the system base and hub to reveal the inner workings of one example of a spring-cam counterbalance system 602. The system uses a tension member in the form of a cable 700 that is attached to the end of the arcuate track 226 at connection point 702. The cable system indirectly connects to spring 726, which provides a force to counterbalance the torque generated by the relevant components masses about the remote-center-of-motion.

In this arrangement the cable 700 is attached to the cable attachment point 702 located on the arcuate track 226. As the cable 700 enters the revolute joint, the cable is redirected vertically by a guide member/pulley 706 located in the housing of the inner revolute 280. The pulley 706 is preferably positioned such that this section of the cable 700 is parallel to the rotation axis 284 and more preferably so that the section of the cable 700 is coaxial with the rotation axis 284 and passes through the center of the revolute joint/hub. This arrangement may help reduce and/or prevent the generation of torque about the revolute joint axis 284 by the arc counterbalance system 602. The cable 700 then passes through the D-profile shaft 348, which is preferably hollow, and is redirected again by a second guide member/pulley 708 located in the housing of outer revolute 282. The cable 700 is wrapped around a cable guide on cam 720 and terminated on cam 720. The cam 720 is rigidly connected to camshaft 712. A second cable 722 is wrapped around and terminated on cam shaft 712, which includes cable grooves to help guide cable 712. The other end of cable 722 is connected to an extension spring 724. The spring 724 is attached to an adjustable spring stud 726, which is attached to the frame 282. The adjustable spring stud 726 is used to make minor adjustments of the location of the spring to ensure proper cable tension in the system. In the preferred embodiment, two springs 724 are used to generate sufficient counterbalance force.

Figure 33:
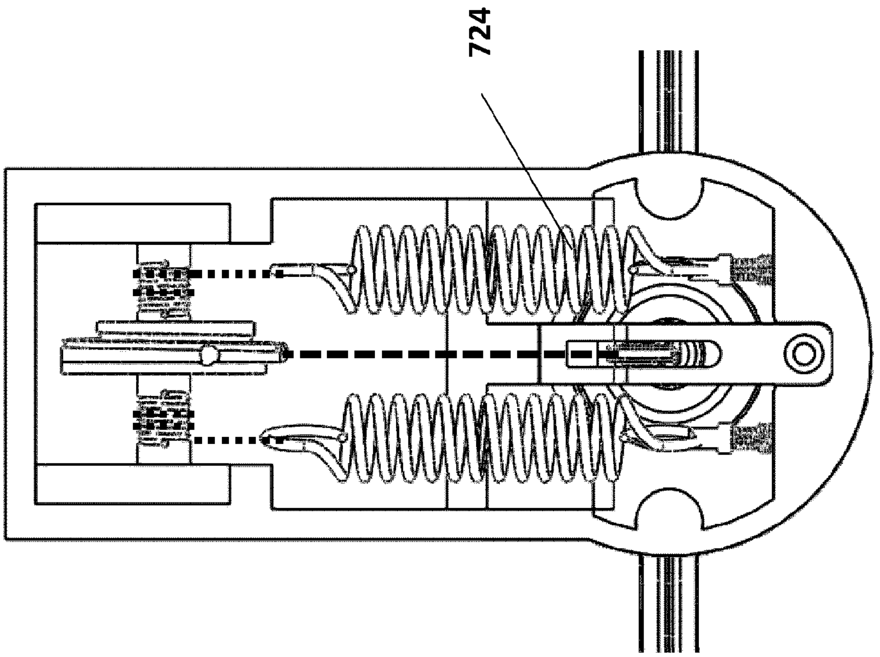
FIG. 32-33 are section views showing one example of a spring-cam counterbalance system for the surgical system.
Figure 32:
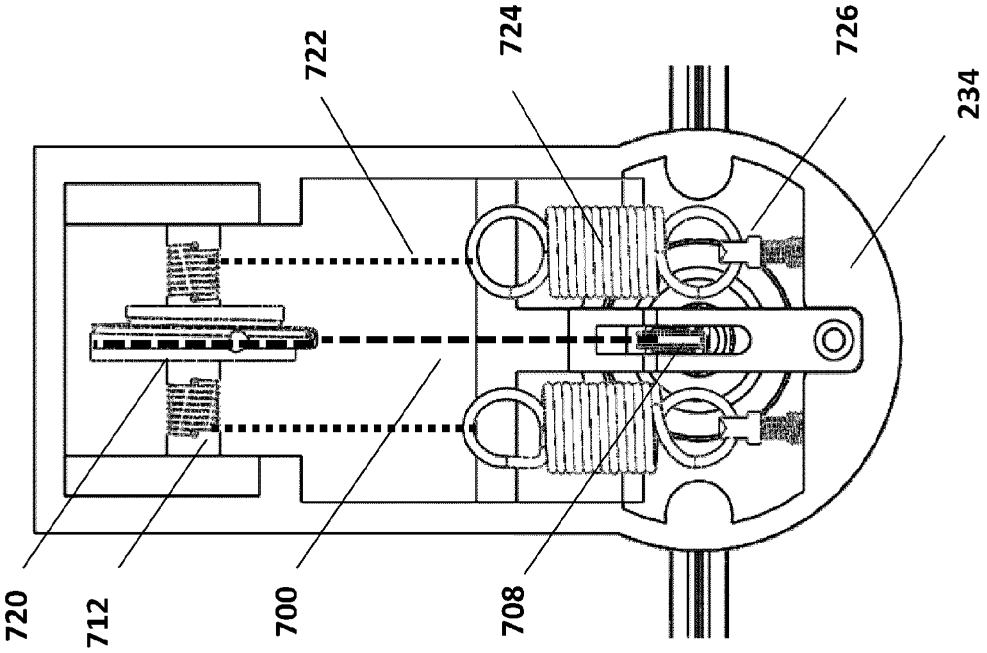

FIG. 30 shows the system as the arcuate track is fully retracted (small θ). As the surgeon moves the handle down, the torque generated by the mass of the system increases. The movement of the arcuate track causes cable 700 to extend and unwrap from cam 720. The rotation of cam 720 and camshaft 712 cause cable 722 to wrap and effectively shorten to pull on spring 724. The simultaneous unwrapping of cable 700 and wrapping of cable 722 caused by the same rotation is achieved by feeding the respective cables to opposite sides of the cam/camshaft. FIG. 31 shows the resulting extended springs when arcuate track 226 is fully extended (large θ). FIG. 32-33 show a top view of the cable system and extension springs.

The counterbalancing systems can work as follows, for example: when the surgeon moves the handle 108 down in the vertical direction, θ increases, thus increasing the torque generated about the remote-center-of-motion 162 due to gravity. As this occurs, the cable 700, which is routed up along the arcuate track and through the revolute joint, generates a torque on cam 720 causing it to rotate and feed additional cable to accommodate the increase in arc length. Simultaneously, as the cam 720 rotates, it turns the camshaft 712 to which it is fixed. The rotating camshaft 712 causes attached cable 722 to shorten and wrap around the camshaft 712. As cable 722 shortens, it pulls on the spring 724. In summary, as θ increases, the cable system causes the spring to extend. The spring force increases the tension in cable 700, which generates a torque in the opposite direction of the torque generated by the mass of the relevant components due to gravity. Conversely, if the surgeon moves the handle 108 in the opposite direction, reducing θ, the spring restoring force causes the camshaft 712 to rotate in the opposite direction and allowing the excess cable 700 to be wound around the cam 720. At any angle θ, the torque generated by the counterbalance system and the torque generated by the mass of the components should be equivalent for the surgical system to be properly counterbalanced; in other words, the torque generated by the spring and by the mass of the relevant systems are preferably equal (or preferably within at least within about 5%, 10%, 15%, 20% or about 25% of each other)

Figure 34C:
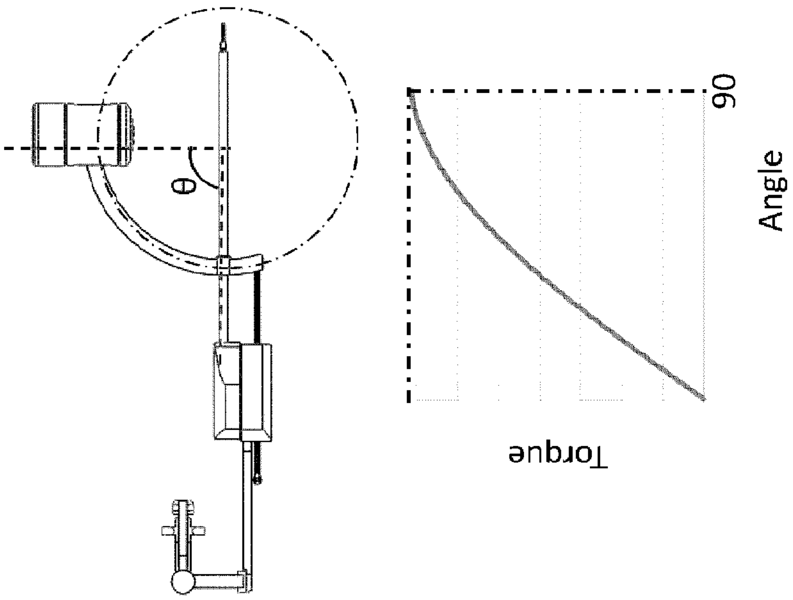
FIGS. 34*a*-34*c* are examples of the sinusoidal torque generated when using the surgical system.
Figure 34B:
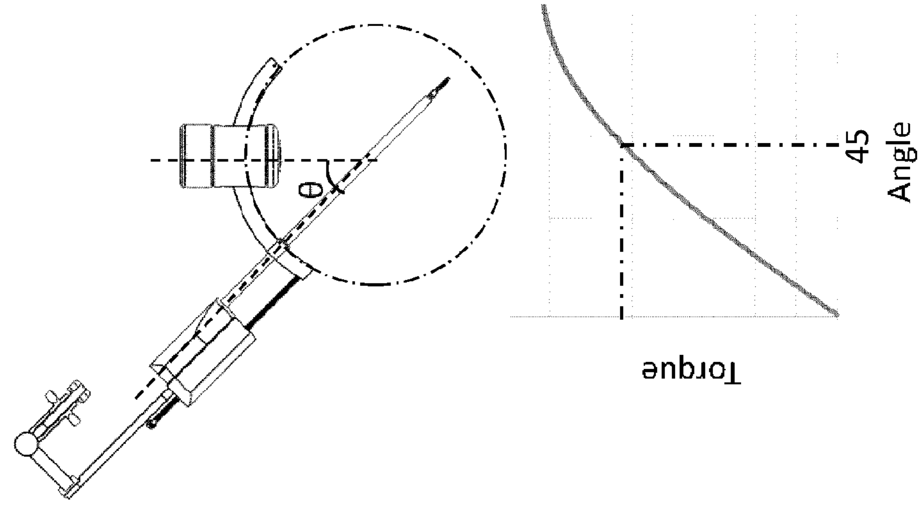
Figure 34A:
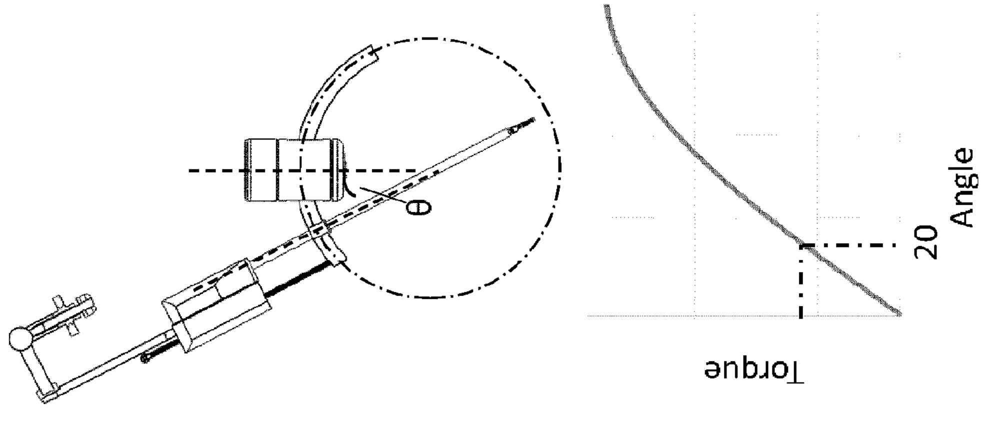

FIGS. 34*a*-34*c* illustrate the profile of the torque generated about the remote-center-of-motion depending on the angle θ. Since the instrument center of mass rotates about the remote-center-of-motion 162, the torque generated increases sinusoidally. At 0-degrees θ, the torque generated is zero, and reaches a maximum at 90-degrees θ. Theoretically, the torque continues to decrease from the peak at 90-degrees θ until it reaches zero again at 180-degrees θ, as it is a function of the lateral distance from the center-of-mass to the vertical axis passing through the remote-center-of-motion 162. To match this sinusoidal torque generated about the remote-center-of-motion 162, the spring 724 must generate a matching sinusoidal counterbalancing force using a specific winding cam 720 having a pre-determine balancing cam profile.

For example, a circular cam with an attached cable and rotating to pull on a linear compression spring will generate a linear torque, as the cable length increases linearly with each degree rotated while the torque arm based on the cam diameter remains constant. The torque generated about the cam's shaft is a product of both the cumulative cable length pulling on the spring and the instantaneous moment arm from the cable to the center of the shaft. Therefore, these two factors that can be considered when generating a non-linear torque about the cam. In the preferred embodiment, the cam 720 has a profile that is shaped such that the product of the cumulative cable length and the moment arm create a sinusoidal torque to match, or at least substantially match, the sinusoidal torque generated as the surgical instrument moves about the arcuate track 224, as shown in FIG. 43.

Alternative embodiments of the described counterbalance system may use a mass instead of a spring system for the counterbalance system contained in the base.

In the examples described herein the arcuate track and the linear track shown as forming part of the translation apparatus are shown as substantially rigid, fixed-length members that are self-supporting and whose configuration remains generally constant while the system and stabilizing apparatus are in use. In this example the movement of the tracks and/or translation of the system components is achieved by sliding or translating one piece along the length of the respective track using a movable carriage or shuttle member as described. In such an arrangement the device attachment unit may, for example be adjacent the distal/free end of the linear track when the surgical device is retracted away from the patient, and may then move away from the free end of the track and toward the fixed end of the linear track that is connected to the arcuate track when the surgical device is moved toward the patient.

Alternatively, and optionally, at least one of these tracks may have a variable length and may change in length while the apparatus is in use. This may facilitate movement of the device attachment unit by changing the length or configuration of these tracks rather than translating along the tracks. For example, the linear translation apparatus may include a linear support member that can shorten and extend its length in the direction of the translation axis. The device attachment unit may be connected to a distal end of the variable length support and may then be moved toward and away from the arcuate support member (along the translation axis) as the distal end of the variable length support itself moves toward and away from the arcuate support member (rather than translating along the linear track). A variable length support may have any suitable configuration, including having two or more telescoping sections, a compressible and/or extensible section, sliding or nested members and the like. The arcuate support may be similarly configured to have a variable length (e.g. a variable arc length) that can be, for example, retracted to move the linear translation apparatus toward the hub and extended to move the linear translation apparatus toward away from the hub.

Figure 35:
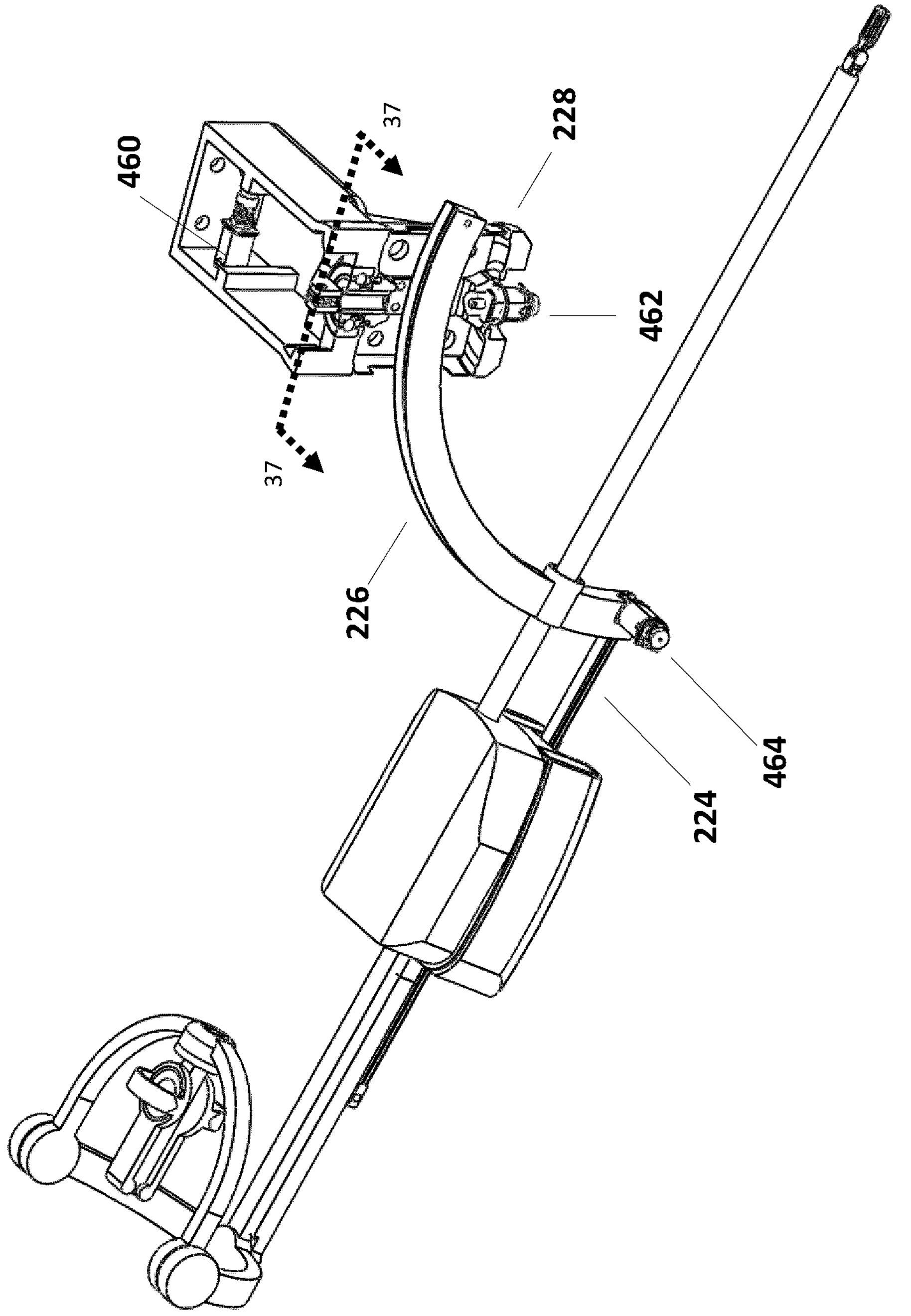
FIG. 35 is an example of the surgical system where powered actuators are used for the counterbalance system.

FIG. 35 shows an example of the counterbalancing method through the use of powered actuators, in this example motors 460 and 464. To apply a biasing force for the linear translation apparatus, motor 464 would be attached to a cable similar to 660. To enable manual manipulation of the moveable components, the motor would be backdriveable and apply a specified torque based on the position of the joints in order to compensate for the weight of the components but without affecting the position during manual manipulation. Motor 460 would have a similar function for compensating for the arcuate track joint. This embodiment enables a hold position mode which would restrict movement of the joints by maintaining the motor positions. This would likely be used during instrument exchanges and other cases during a surgical procedure where the device should not move.

Additionally, non-powered counterbalance mechanisms can be used in combination with powered actuators to reduce the load on the actuators while enhancing the safety. In one such example, the non-powered counterbalance mechanisms would at least partially counterbalance the weight of the moving components. In the case that the powered actuators are motors, this would reduce their torque requirements. The powered actuators could drive the individual joints to achieve automatic positioning or be used to maintain a specific position. Having the non-powered counterbalance mechanisms substantially counteract the weight of the moving components would add a level of safety during a power fault.

Figure 36:
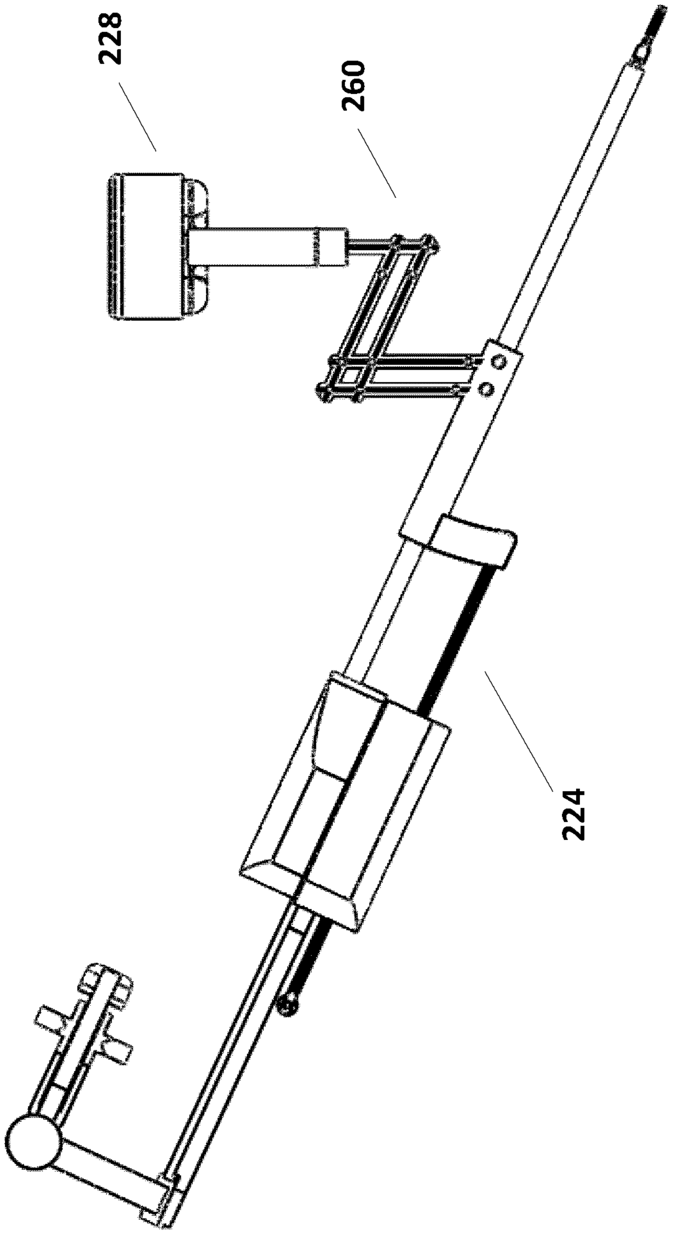
FIG. 36 depicts an example of the surgical system where a parallelogram structure is used for the stabilizing apparatus to create a remote center of motion.

FIG. 36 illustrates an alternative example of the surgical system in which the arcuate track is replaced with an alternative structure that includes a parallelogram structure 260, having a plurality of movably connected linkage members. One end of the parallelogram structure 260 connects to the rotatable hub and the other connects to and supports the translation apparatus (e.g. linear track 224). The parallelogram structure 260 can enables a remote axis of rotation for the surgical device port in the same manner as the arcuate track described in other examples. The resulting axis of the parallelogram can be counterbalanced using a similar cable and spring based approach shown in FIG. 31 or using powered actuators as shown in FIG. 35.

As described herein, the surgical system may optionally be configured to also operate in a companion mode in addition to its primary mode. For example, if the surgical system is configured as shown in FIG. 1 it may include three robotic surgical units 104, 106 and 120 with corresponding stabilizing apparatuses, with two units 104 and 106 being used to hold for surgical instrumentation and one unit 120 configured to hold an endoscopic camera. In this arrangement a surgeon may have their hands on handles 108 and 110 for two wristed instruments and it may be desirable to allow that surgeon to also control a companion endoscope unit, preferably with the stabilizing apparatus of endoscope unit being drivable by powered actuators, then the surgeon could control the position of the endoscope from the handle they are already grasping and an assistant (or other user) may not be required for positioning. Activating this type of companion mode may be done by pressing a button or other such auxiliary input device on either handle to switch between control of the local, wristed end-effector that the handle is physically attached to and positioning the separate endoscope.

This type of companion mode may be preferable over conventional, standalone motorized endoscope positioners that may require separate input mechanisms such as voice commands, foot pedals, or head tilts for control (since the surgeon has their hands on their instruments). In contrast, the systems described herein may help the surgeon control the position of a companion device, such as the endoscope through their hand movements on the primary device handles.

Figure 37:
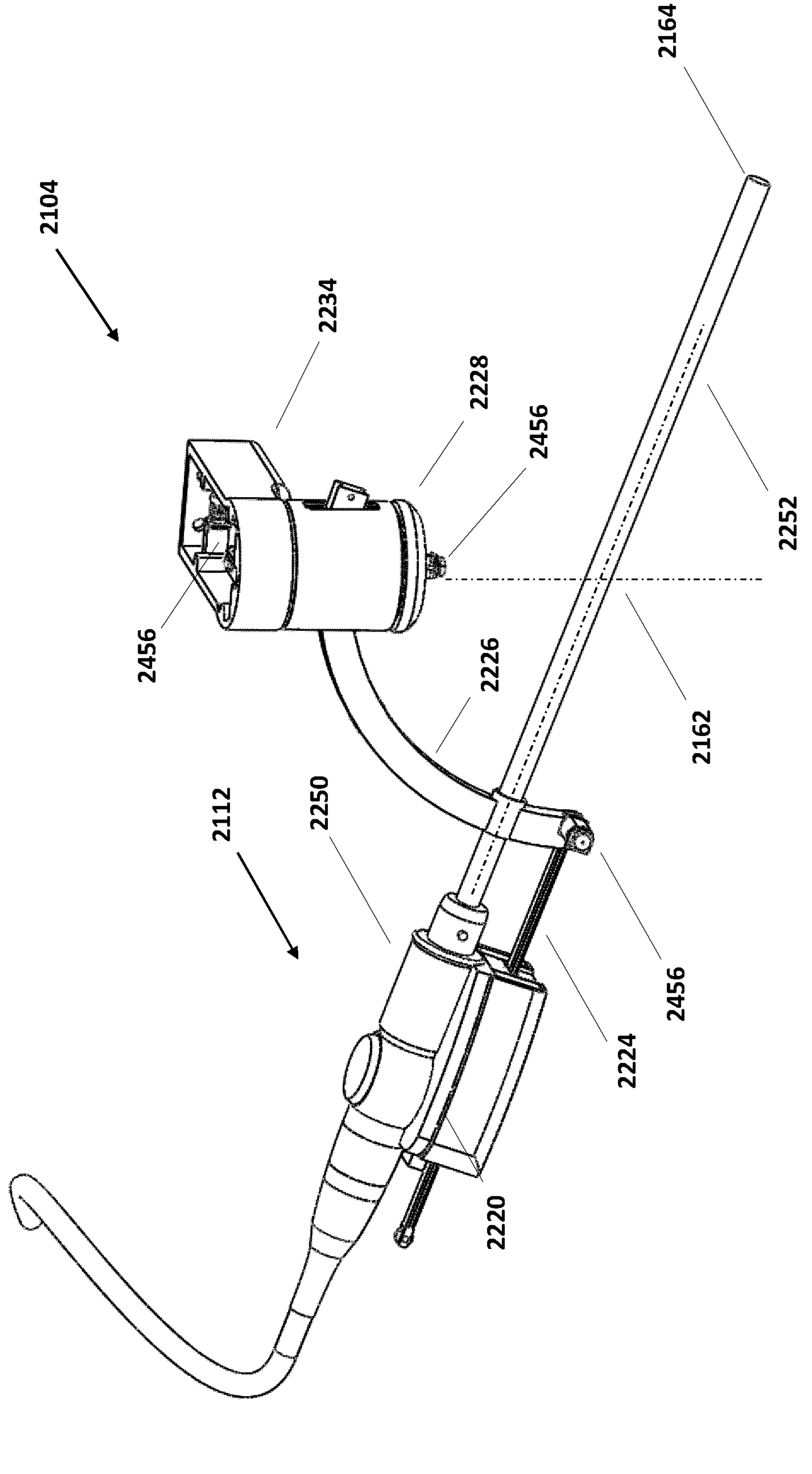
FIG. 37 is an example of the surgical system where the attached surgical device is an endoscope.
Figure 38:
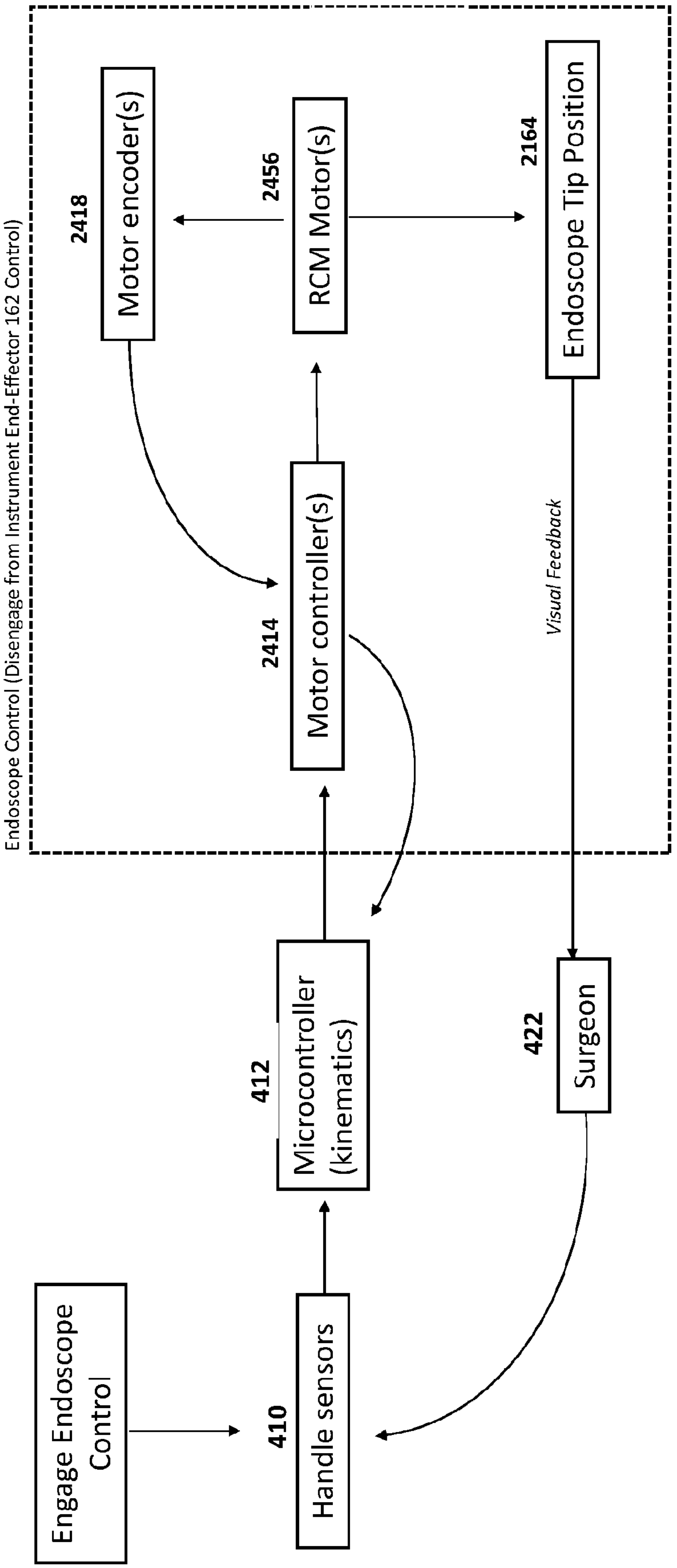
FIG. 38 is a flow chart illustrating one example of a control schematic for operating a surgical system in a companion mode.

Referring to FIG. 37 one example of second/companion remote center of motion mechanism 2104 includes with an attached endoscope 2112 comprised of a base 2250, shaft 2162, and distal end 2164. The endoscope base 2250 is removably attached to a mating connection interface 2220 on the second device attachment unit. This example of the stabilizing apparatus is not a passive apparatus as it has a companion powered drive system that may include motors 2456 and/or other suitable powered actuators that can be communicably linked to the controller (such as controller 412) of a separate, primary stabilizing apparatus. In this arrangement powered drive system can be used to move portions of the stabilizing apparatus to help move the device attachment unit 2220 and the endoscope 2112 may be positioned in response to inputs from the primary control handle (such as handle 108 and 1108). FIG. 38 shows one schematic example of a control system for a surgical system that includes a companion mode. In this arrangement, when the system is switched into companion mode—e.g. for endoscope control—the handle sensors 410 and controller 412 can be connected (via wires, wireless protocol, etc.) to the separate motor controllers 2414 to control motors 2456 (with optional feedback provided via encoders 2418) and thereby control the position of the tip of the endoscope (with optional feedback provided via tip position encoders 2164). When endoscope 2112 is in its desired position the system can be returned to its primary operating mode and using the control scheme as shown in FIG. 17 (or other suitable systems).

While this description includes references to illustrative embodiments and examples, the description is not intended to be construed in a limiting sense. Thus, various modifications of the illustrative embodiments, as well as other embodiments of the invention(s) described herein, will be apparent to persons skilled in the art upon reference to this description. It is therefore contemplated that the appended claims will cover any such modifications or embodiments.

All publications, patents and patent applications referred to herein are incorporated by reference in their entirety to the same extent as if each individual publication, patent, or patent application was specifically and individually indicated to be incorporated by reference in its entirety.

What is claimed is:

1. A hybrid, direct-control and robotic-assisted surgical system comprising:
- a stabilizing apparatus configured to at least partially passively support a weight of a surgical device, the stabilizing apparatus comprising:
  - a base member configured to be fixed relative to a patient during manipulation of the surgical device,
  - a device attachment unit that is movable relative to the base member and configured to removably receive the surgical device having an elongate shaft and a distal tip,
  - three joints: a revolute joint, a remote center of motion joint, and a prismatic joint, wherein a rotational angle of the revolute joint is substantially aligned with a gravity vector, and
  - a translation counterbalance system configured to counterbalance gravity loads on, at least, the device attachment unit and the surgical device, and an arc counterbalance system for the remote center of motion joint configured to counterbalance torque about a point defined by the stabilizing apparatus; and
- a handle rigidly coupled to the device attachment unit and configured to move relative to the base member to cause a corresponding movement of the distal tip of the surgical device when received in the device attachment unit.

2. The system of claim 1, wherein the stabilizing apparatus is configured to constrain movement of the surgical device to a predetermined range of motion in one or more degrees of freedom.

3. The system of claim 1, further comprising the surgical device having the elongate shaft comprising the distal tip comprising an end effector.

4. The system of claim 1, wherein the translation counterbalance system comprises a counterweight, wherein:
- when the device attachment unit is translated in a first direction, the counterweight translates in an opposite direction to counterbalance the device attachment unit, the handle and the surgical device,
- when the surgical device is attached to the device attachment unit, a combined linear centre of mass of the device attachment unit, the handle, the surgical device and the counterweight is located at a reference position relative to the point defined by the stabilizing apparatus, and
- the combined linear centre of mass substantially remains in the reference position with respect to the linear translation apparatus when the device attachment unit and the counterweight translate along the linear translation apparatus.

5. The system of claim 1, wherein the prismatic joint includes a linear translation apparatus comprising a linear track coupled to the stabilizing apparatus and extending to a free end axially spaced apart from the stabilizing apparatus, and wherein the device attachment unit is slidably connected to the linear track and translatable along the linear track.

6. The system of claim 1, wherein the point defined by the stabilizing apparatus is a remote centre of motion or a pivot point for minimally invasive surgery.

7. The system of claim 1, wherein:
- the revolute joint includes a hub rotatably connected to the base and rotatable about a rotation axis, and
- the remote center of motion joint includes a parallelogram structure connected to the hub.

8. The system of claim 1, wherein:
- the revolute joint includes a hub rotatably connected to the base and rotatable about a rotation axis, and
- the remote center of motion joint includes an arcuate track connected to the hub.

9. The system of claim 1, wherein the device attachment unit is movable relative to the base member in response to a manual input from a user and without engaging a drive mechanism while the system is in use.

10. The system of claim 1, further comprising a companion surgical device communicably connected to a controller and the handle, wherein the handle, via the controller, is configured to control the surgical device coupled to the device attachment unit and the companion surgical device.

11. The system of claim 10, wherein, when the system is in a companion mode, the controller does not generate a primary control signal whereby movements of the handle do not actuate an end effector of the surgical device received in the device attachment unit.

* * * * *